(12) United States Patent
Mishra et al.

(10) Patent No.: US 7,041,705 B2
(45) Date of Patent: May 9, 2006

(54) INJECTABLE AQUEOUS DISPERSIONS OF PROPOFOL

(75) Inventors: Awadhesh K. Mishra, Brossard (CA); Gary W. Pace, Winchester, MA (US); Michael G Vachon, Westmount (CA)

(73) Assignee: Jagotec AG, Muttenz (CH)

( * ) Notice: Subject to any disclaimer, the term of this patent is extended or adjusted under 35 U.S.C. 154(b) by 680 days.

(21) Appl. No.: 09/820,371

(22) Filed: Mar. 26, 2001

(65) Prior Publication Data

US 2002/0006442 A1    Jan. 17, 2002

Related U.S. Application Data

(62) Division of application No. 09/376,487, filed on Aug. 18, 1999.

(60) Provisional application No. 60/097,071, filed on Aug. 19, 1998.

(51) Int. Cl.
*A01N 31/08*    (2006.01)
*A61K 31/05*    (2006.01)

(52) U.S. Cl. .................... 514/731; 514/816; 514/817; 514/818; 514/938; 424/400

(58) Field of Classification Search .............. 424/405; 514/816–818, 938
See application file for complete search history.

(56) References Cited

U.S. PATENT DOCUMENTS

| | | | |
|---|---|---|---|
| 2,803,582 A | 8/1957 | Cherney | |
| 3,137,631 A | 6/1964 | Soloway | |
| 3,216,897 A | 11/1965 | Krantz et al. | |
| 3,274,063 A | 9/1966 | Nieper et al. | |
| 3,440,318 A | 4/1969 | Polin | |
| 3,594,476 A | 7/1971 | Merrill | |
| 3,715,432 A | 2/1973 | Merrill | |
| 3,755,557 A | 8/1973 | Jacobs | |
| 3,776,857 A | 12/1973 | Lindner | |
| 3,794,476 A | 2/1974 | Michalik et al. | |
| 3,937,668 A | 2/1976 | Zolle | |
| 3,960,757 A | 6/1976 | Morishita et al. | |
| 3,965,255 A | 6/1976 | Bloch et al. | |
| 4,016,100 A | 4/1977 | Suzuki et al. | |
| 4,053,585 A | 10/1977 | Allison et al. | |
| 4,056,635 A | 11/1977 | Glen et al. | |
| 4,073,943 A | 2/1978 | Wretlind et al. | |
| 4,078,052 A | 3/1978 | Papahadjopoulos | |
| 4,089,801 A | 5/1978 | Schneider | |
| 4,102,806 A | 7/1978 | Kondo et al. | |
| 4,107,288 A | 8/1978 | Oppenheim et al. | |
| 4,133,874 A | 1/1979 | Miller et al. | |
| 4,145,410 A | 3/1979 | Sears | |
| 4,147,767 A | 4/1979 | Yapel, Jr. | |
| 4,168,308 A | 9/1979 | Wretlind et al. | |
| 4,186,183 A | 1/1980 | Steck et al. | |
| 4,219,548 A | 8/1980 | Reller | |
| 4,235,871 A | 11/1980 | Papahadjopoulos et al. | |
| 4,241,046 A | 12/1980 | Papahadjopoulos et al. | |
| 4,271,196 A | 6/1981 | Schmidt | |
| 4,280,996 A | 7/1981 | Okamoto et al. | |
| 4,298,594 A | 11/1981 | Sears et al. | |
| 4,302,459 A | 11/1981 | Steck et al. | |
| 4,308,166 A | 12/1981 | Marchetti et al. | |
| 4,309,421 A | 1/1982 | Ghyczy et al. | |
| 4,316,884 A | 2/1982 | Alam et al. | |
| 4,320,121 A | 3/1982 | Sears | |
| 4,325,871 A | 4/1982 | Sasaki et al. | |
| 4,328,222 A | 5/1982 | Schmidt | |
| 4,329,332 A | 5/1982 | Couvreur et al. | |
| 4,331,654 A | 5/1982 | Morris | |
| 4,332,795 A | 6/1982 | Ghyczy et al. | |
| 4,332,796 A | 6/1982 | Los | |
| 4,340,594 A | 7/1982 | Mizushima et al. | |
| 4,345,588 A | 8/1982 | Widder et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,378,354 A | 3/1983 | Ghyczy et al. | |
| 4,394,182 A | 7/1983 | Maddox, III | |
| 4,394,372 A | 7/1983 | Taylor | |
| 4,397,372 A | 8/1983 | DeKraker | |
| 4,397,846 A | 8/1983 | Weiner et al. | |
| 4,411,894 A | 10/1983 | Schrank et al. | |
| 4,411,933 A | 10/1983 | Samejima et al. | |
| 4,421,747 A | 12/1983 | Ghyczy et al. | |
| 4,427,649 A | 1/1984 | Dingle et al. | |

(Continued)

FOREIGN PATENT DOCUMENTS

DE    25 13 797    10/1975

(Continued)

OTHER PUBLICATIONS

Cox et al "Influence of different fat emulsion . . . " Pharmaceutical Research vol. 15, No. 3, Mar. 1998, pp. 442-448.

(Continued)

*Primary Examiner*—Michael Hartley
*Assistant Examiner*—Nabila Ebrahim
(74) *Attorney, Agent, or Firm*—Mintz Levin Cohn Ferris Glovsky and Popeo, P.C.

(57)  ABSTRACT

Irritation upon injection of a formulation containing propofol is reduced or substantially eliminated by administering a stable, sterile, and antimicrobial aqueous dispersion comprising a water-insoluble microdroplet matrix of mean diameter from about 50 nm to about 1000 nm consisting essentially of about 1% to about 15% of propofol, up to about 7% of a propofol-soluble diluent, and about 0.8% to about 4% of a surface stabilizing amphiphilic aent. The aqueous phase includes a pharmaceutically acceptable water-soluble polyhydroxy tonicity modifier. The propofol-containing dispersion is devoid of additional bactericidal or bacteriostatic preservative agents.

91 Claims, No Drawings

U.S. PATENT DOCUMENTS

| | | | |
|---|---|---|---|
| 4,448,765 A | 5/1984 | Ash et al. | |
| 4,452,817 A | 6/1984 | Glen et al. | |
| 4,474,753 A | 10/1984 | Haslam et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,522,803 A | 6/1985 | Lenk et al. | |
| 4,529,561 A | 7/1985 | Hunt et al. | |
| 4,532,089 A | 7/1985 | MacDonald | |
| 4,588,578 A | 5/1986 | Fountain et al. | |
| 4,610,868 A | 9/1986 | Fountain et al. | |
| 4,613,505 A | 9/1986 | Mizushima et al. | |
| 4,614,702 A | 9/1986 | Sawada et al. | |
| 4,622,219 A | 11/1986 | Haynes | |
| RE32,393 E | 4/1987 | Wretlind et al. | |
| 4,675,236 A | 6/1987 | Ohkawara et al. | |
| 4,687,762 A | 8/1987 | Fukushima et al. | |
| 4,711,902 A | 12/1987 | Serno | |
| 4,719,239 A | 1/1988 | Muller et al. | |
| 4,725,442 A | 2/1988 | Haynes | |
| 4,756,910 A | 7/1988 | Yagi et al. | |
| 4,761,228 A | 8/1988 | Weisenbarger et al. | |
| 4,762,720 A | 8/1988 | Jizomoto | |
| 4,766,046 A | 8/1988 | Abra et al. | |
| 4,776,991 A | 10/1988 | Farmer et al. | |
| 4,798,846 A | 1/1989 | Glen et al. | |
| 4,798,860 A | 1/1989 | Parr | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,837,028 A | 6/1989 | Allen | |
| 4,839,111 A | 6/1989 | Huang | |
| 4,863,737 A | 9/1989 | Stanley et al. | |
| 4,863,740 A | 9/1989 | Kissel et al. | |
| 4,880,634 A | 11/1989 | Speiser | |
| 4,895,726 A | 1/1990 | Curtet et al. | |
| 4,937,078 A | 6/1990 | Mezei et al. | |
| 4,961,890 A | 10/1990 | Boyer | |
| 4,963,362 A | 10/1990 | Rahman et al. | |
| 4,963,367 A | 10/1990 | Ecanow | |
| 4,973,465 A | 11/1990 | Baurain et al. | |
| 5,004,612 A | 4/1991 | Kim et al. | |
| 5,023,087 A | 6/1991 | Yau-Young | |
| 5,028,600 A | 7/1991 | Jeppsson | |
| 5,030,453 A | 7/1991 | Lenk et al. | |
| 5,049,388 A | 9/1991 | Knight et al. | |
| 5,091,187 A | 2/1992 | Haynes | |
| 5,091,188 A | 2/1992 | Haynes | |
| 5,098,606 A | 3/1992 | Nakajima et al. | |
| 5,100,591 A | 3/1992 | Leclef et al. | |
| 5,118,493 A | 6/1992 | Kelley et al. | |
| 5,128,147 A | 7/1992 | Leveen et al. | |
| 5,132,114 A | 7/1992 | Stanley et al. | |
| 5,133,965 A | 7/1992 | Fountain | |
| 5,145,684 A | 9/1992 | Liversidge et al. | |
| 5,147,884 A | 9/1992 | Diehl et al. | |
| 5,152,923 A | 10/1992 | Weder et al. | |
| 5,167,950 A | 12/1992 | Lins | |
| 5,179,079 A | 1/1993 | Hansen et al. | |
| 5,188,837 A | 2/1993 | Domb | |
| 5,217,707 A | 6/1993 | Szabo et al. | |
| 5,227,165 A | 7/1993 | Domb et al. | |
| 5,234,634 A | 8/1993 | Janoff et al. | |
| 5,234,767 A | 8/1993 | Wallach | |
| 5,244,925 A | 9/1993 | Wretlind et al. | |
| 5,246,707 A | 9/1993 | Haynes | |
| 5,256,422 A | 10/1993 | Albert et al. | |
| 5,256,641 A | 10/1993 | Yatvin et al. | |
| 5,264,207 A | 11/1993 | Bommelaer et al. | |
| 5,269,979 A | 12/1993 | Fountain | |
| 5,288,497 A | 2/1994 | Stanley et al. | |
| 5,288,498 A | 2/1994 | Stanley et al. | |
| 5,294,604 A | 3/1994 | Nussenblatt et al. | |
| 5,298,262 A | 3/1994 | Na et al. | |
| 5,302,401 A | 4/1994 | Liversidge et al. | |
| 5,308,874 A | 5/1994 | Sanchez et al. | |
| 5,314,915 A | 5/1994 | Rencher | |
| 5,320,906 A | 6/1994 | Eley et al. | |
| 5,326,552 A | 7/1994 | Na et al. | |
| 5,332,576 A | 7/1994 | Mantelle | |
| 5,336,507 A | 8/1994 | Na et al. | |
| 5,338,761 A | 8/1994 | Nakajima et al. | |
| 5,340,588 A | 8/1994 | Domb | |
| 5,346,702 A | 9/1994 | Na et al. | |
| 5,352,459 A | 10/1994 | Hollister et al. | |
| 5,364,633 A | 11/1994 | Hill et al. | |
| 5,376,646 A | 12/1994 | Pittrof et al. | |
| 5,378,451 A | 1/1995 | Gorman et al. | |
| 5,389,377 A | 2/1995 | Chagnon et al. | |
| 5,399,363 A | 3/1995 | Liversidge et al. | |
| 5,407,609 A | 4/1995 | Tice et al. | |
| 5,409,698 A | 4/1995 | Anderson et al. | |
| 5,429,824 A | 7/1995 | June | |
| 5,446,070 A | 8/1995 | Mantelle | |
| 5,447,710 A | 9/1995 | Na et al. | |
| 5,451,408 A | 9/1995 | Mezei et al. | |
| 5,461,080 A | 10/1995 | Sanchez et al. | |
| 5,478,860 A | 12/1995 | Wheeler et al. | |
| 5,496,537 A | 3/1996 | Henry | |
| 5,496,811 A | 3/1996 | Aviv et al. | |
| 5,496,818 A | 3/1996 | Schaupp et al. | |
| 5,498,420 A | 3/1996 | Mentrup Edgar et al. | |
| 5,498,421 A | 3/1996 | Grinstaff et al. | |
| 5,508,275 A | 4/1996 | Weithmann et al. | |
| 5,510,118 A | 4/1996 | Bosch et al. | |
| 5,518,187 A | 5/1996 | Bruno et al. | |
| 5,518,730 A | 5/1996 | Fuisz | |
| 5,527,537 A | 6/1996 | Dietl | |
| 5,534,270 A | 7/1996 | De Castro | |
| 5,536,413 A | 7/1996 | Bormann et al. | |
| 5,545,628 A | 8/1996 | Deboeck et al. | |
| RE35,338 E | 9/1996 | Haynes | |
| 5,556,580 A | 9/1996 | Suddith | |
| 5,560,931 A | 10/1996 | Eickhoff et al. | |
| 5,569,464 A | 10/1996 | Endo et al. | |
| 5,571,536 A | 11/1996 | Eickhoff et al. | |
| 5,576,012 A | 11/1996 | Bauer et al. | |
| 5,576,016 A | 11/1996 | Amselem et al. | |
| 5,589,455 A | 12/1996 | Woo | |
| 5,589,508 A | 12/1996 | Schlotzer et al. | |
| 5,589,598 A | 12/1996 | Paiocchi | |
| 5,591,311 A | 1/1997 | Ramachandran | |
| 5,603,951 A | 2/1997 | Woo | |
| 5,607,694 A | 3/1997 | Marx | |
| 5,618,522 A | 4/1997 | Kaleta et al. | |
| 5,618,563 A | 4/1997 | Berde et al. | |
| 5,626,869 A | 5/1997 | Nyqvist et al. | |
| 5,631,019 A | 5/1997 | Marx | |
| 5,635,203 A | 6/1997 | Gale et al. | |
| 5,635,205 A | 6/1997 | Nyqvist et al. | |
| 5,635,536 A | 6/1997 | Lyons | |
| 5,635,540 A | 6/1997 | Edlich et al. | |
| 5,637,625 A | 6/1997 | Haynes | |
| 5,639,474 A | 6/1997 | Woo | |
| 5,641,508 A | 6/1997 | Li et al. | |
| 5,645,856 A | 7/1997 | Lacy et al. | |
| 5,648,375 A | 7/1997 | Abraham | |
| 5,651,982 A | 7/1997 | Marx | |
| 5,651,991 A | 7/1997 | Sugiyama et al. | |
| 5,656,280 A | 8/1997 | Herb et al. | |

| | | | | | |
|---|---|---|---|---|---|
| 5,656,286 A | 8/1997 | Miranda et al. | 5,945,510 A | 8/1999 | Fasano |
| 5,656,289 A | 8/1997 | Cho et al. | 5,958,379 A | 9/1999 | Regenold et al. |
| 5,658,583 A | 8/1997 | Zhang et al. | 5,958,449 A | 9/1999 | Hersch et al. |
| 5,660,837 A | 8/1997 | Lundquist | 5,962,536 A | 10/1999 | Komer |
| 5,660,854 A | 8/1997 | Haynes et al. | 5,972,366 A | 10/1999 | Haynes et al. |
| 5,660,858 A | 8/1997 | Parikh et al. | 5,972,938 A | 10/1999 | Rupniak et al. |
| 5,662,932 A | 9/1997 | Amselem et al. | 5,980,936 A | 11/1999 | Krafft et al. |
| 5,665,380 A | 9/1997 | Wallach et al. | 5,990,176 A | 11/1999 | Bieniarz et al. |
| 5,665,700 A | 9/1997 | Cho et al. | 5,993,850 A | 11/1999 | Sankaram et al. |
| 5,667,809 A | 9/1997 | Trevino et al. | 5,994,318 A | 11/1999 | Gould-Fogerite et al. |
| 5,677,341 A | 10/1997 | Lyons | 6,004,566 A | 12/1999 | Friedman et al. |
| 5,686,102 A | 11/1997 | Gross et al. | 6,004,962 A | 12/1999 | Gooberman |
| 5,688,528 A | 11/1997 | Carlsson et al. | 6,011,067 A | 1/2000 | Hersh |
| 5,693,337 A | 12/1997 | Suzuki et al. | 6,013,665 A | 1/2000 | DeMichele et al. |
| 5,700,482 A | 12/1997 | Frederiksen et al. | 6,017,513 A | 1/2000 | Betbeder et al. |
| 5,705,039 A | 1/1998 | Clarke et al. | 6,019,997 A | 2/2000 | Scholz et al. |
| 5,714,520 A | 2/1998 | Jones et al. | 6,022,547 A | 2/2000 | Herb et al. |
| 5,719,197 A | 2/1998 | Kanios et al. | 6,024,976 A | 2/2000 | Miranda et al. |
| 5,731,355 A | 3/1998 | Jones et al. | 6,025,362 A | 2/2000 | Fukunaga et al. |
| 5,731,356 A | 3/1998 | Jones et al. | 6,028,066 A | 2/2000 | Unger |
| 5,733,572 A | 3/1998 | Unger et al. | 6,028,108 A | 2/2000 | George |
| 5,747,060 A | 5/1998 | Sackler et al. | 6,031,007 A | 2/2000 | Brodin et al. |
| 5,750,137 A | 5/1998 | Taskovich et al. | 6,046,163 A | 4/2000 | Stuchlik et al. |
| 5,750,142 A | 5/1998 | Friedman et al. | 6,046,187 A | 4/2000 | Berde et al. |
| 5,753,258 A | 5/1998 | Schreier et al. | 6,054,421 A | 4/2000 | Lyons et al. |
| 5,756,120 A | 5/1998 | Hersch et al. | 6,057,289 A | 5/2000 | Mulye |
| 5,756,121 A | 5/1998 | Bracken | 6,063,762 A | 5/2000 | Hong et al. |
| 5,759,571 A | 6/1998 | Hersch et al. | 6,071,534 A | 6/2000 | Kim et al. |
| 5,766,625 A | 6/1998 | Schreier et al. | 6,071,927 A | 6/2000 | Baker et al. |
| 5,766,627 A | 6/1998 | Sankaram et al. | 6,071,928 A | 6/2000 | Curtis et al. |
| 5,770,222 A | 6/1998 | Unger et al. | 6,071,933 A | 6/2000 | Joo et al. |
| 5,773,026 A | 6/1998 | Schlipalius | 6,071,974 A | 6/2000 | Patel et al. |
| 5,773,106 A | 6/1998 | deGroot et al. | 6,075,059 A | 6/2000 | Reader |
| 5,776,488 A | 7/1998 | Mori et al. | 6,079,416 A | 6/2000 | Williams |
| 5,776,495 A | 7/1998 | Duclos et al. | 6,086,376 A | 7/2000 | Moussa et al. |
| 5,780,045 A | 7/1998 | McQuinn et al. | 6,086,911 A | 7/2000 | Godbey |
| 5,785,976 A | 7/1998 | Westesen et al. | 6,096,338 A | 8/2000 | Lacy et al. |
| 5,785,989 A | 7/1998 | Stanley et al. | 6,100,302 A | 8/2000 | Pejaver et al. |
| 5,785,991 A | 7/1998 | Burkoth et al. | 6,103,269 A | 8/2000 | Wunderlich et al. |
| 5,789,411 A | 8/1998 | Gooberman et al. | 6,106,848 A | 8/2000 | Preuilh et al. |
| 5,807,316 A | 9/1998 | Teeple, Jr. | 6,106,858 A | 8/2000 | Ye et al. |
| 5,807,534 A | 9/1998 | Pomato et al. | 6,113,921 A | 9/2000 | Friedman et al. |
| 5,807,572 A | 9/1998 | Kim et al. | 6,117,066 A | 9/2000 | Abrams et al. |
| 5,807,573 A | 9/1998 | Ljusberg-Wahren et al. | 6,120,797 A | 9/2000 | Meers et al. |
| 5,827,520 A | 10/1998 | de Salvert | 6,121,261 A | 9/2000 | Glatt et al. |
| 5,827,533 A | 10/1998 | Needham | 6,123,923 A | 9/2000 | Unger et al. |
| 5,827,534 A | 10/1998 | Fasano | 6,132,766 A | 10/2000 | Sankaram et al. |
| 5,827,536 A | 10/1998 | Laruelle | 6,140,373 A | 10/2000 | May et al. |
| 5,827,822 A | 10/1998 | Floc'h et al. | 6,140,374 A | 10/2000 | May et al. |
| 5,843,465 A | 12/1998 | Lundquist | 6,147,122 A | 11/2000 | Mirejovsky et al. |
| 5,843,468 A | 12/1998 | Burkoth et al. | 6,150,423 A | 11/2000 | Carpenter |
| 5,843,474 A | 12/1998 | Williams | 6,153,217 A | 11/2000 | Jin et al. |
| 5,853,755 A | 12/1998 | Foldvari | 6,160,007 A | 12/2000 | DeMichele et al. |
| 5,855,908 A | 1/1999 | Stanley et al. | 6,177,477 B1 | 1/2001 | George et al. |
| 5,858,398 A | 1/1999 | Cho | 6,180,136 B1 | 1/2001 | Larson et al. |
| 5,858,401 A | 1/1999 | Bhalani et al. | 6,190,894 B1 | 2/2001 | Thornfeldt et al. |
| 5,858,410 A | 1/1999 | Muller et al. | 6,197,323 B1 | 3/2001 | Georgieff |
| 5,880,148 A | 3/1999 | Edgar et al. | 6,204,257 B1 | 3/2001 | Stella et al. |
| 5,882,676 A | 3/1999 | Lee et al. | 6,217,886 B1 | 4/2001 | Önyüksel et al. |
| 5,885,172 A | 3/1999 | Hebert et al. | 6,221,383 B1 | 4/2001 | Miranda et al. |
| 5,885,597 A | 3/1999 | Botknecht et al. | 6,228,399 B1 | 5/2001 | Parikh et al. |
| 5,908,619 A | 6/1999 | Scholz | 6,232,311 B1 | 5/2001 | Rupniak et al. |
| 5,908,825 A | 6/1999 | Fasano et al. | 6,242,446 B1 | 6/2001 | Glatt et al. |
| 5,908,869 A | 6/1999 | Jones et al. | 6,254,853 B1 | 7/2001 | Hendler et al. |
| 5,912,007 A | 6/1999 | Pan et al. | 6,261,537 B1 | 7/2001 | Klaveness et al. |
| 5,912,271 A | 6/1999 | Brodin et al. | 6,264,917 B1 | 7/2001 | Klaveness et al. |
| 5,916,596 A | 6/1999 | Desai et al. | 6,264,981 B1 | 7/2001 | Zhang et al. |
| 5,922,340 A | 7/1999 | Berde et al. | 6,267,985 B1 | 7/2001 | Chen et al. |
| 5,922,355 A | 7/1999 | Parikh et al. | 6,274,633 B1 | 8/2001 | Franks et al. |
| 5,922,705 A | 7/1999 | Simon | 6,281,175 B1 | 8/2001 | Lyons et al. |
| 5,925,014 A | 7/1999 | Teeple Jr. | 6,281,242 B1 | 8/2001 | Regan et al. |
| 5,932,243 A | 8/1999 | Fricker et al. | 6,284,267 B1 | 9/2001 | Aneja |
| 5,942,497 A | 8/1999 | Fukunaga et al. | 6,288,040 B1 | 9/2001 | Müller et al. |

| | | |
|---|---|---|
| 6,288,127 B1 | 9/2001 | Bieniarz et al. |
| 6,291,013 B1 | 9/2001 | Gibson et al. |
| 6,294,191 B1 | 9/2001 | Meers et al. |
| 6,294,192 B1 | 9/2001 | Patel et al. |
| 6,297,985 B1 | 10/2001 | Kang |
| 6,309,623 B1 | 10/2001 | Weers et al. |
| 6,312,715 B1 | 11/2001 | Cantor et al. |
| 6,322,810 B1 | 11/2001 | Alkan-Onyuksel et al. |
| 6,326,406 B1 | 12/2001 | De Tommaso |
| 6,328,708 B1 | 12/2001 | Georgieff |
| 6,331,289 B1 | 12/2001 | Klaveness et al. |
| 6,332,138 B1 | 12/2001 | Hull et al. |
| 6,350,480 B1 | 2/2002 | Urnezis et al. |
| 6,362,234 B1 | 3/2002 | Hendler |
| 6,365,190 B1 | 4/2002 | Gordon et al. |
| 6,368,619 B1 | 4/2002 | New et al. |
| 6,383,471 B1 | 5/2002 | Chen et al. |
| 6,391,336 B1 | 5/2002 | Royer |
| 6,391,832 B1 | 5/2002 | Lyons et al. |
| 6,399,087 B1 | 6/2002 | Zhang et al. |
| 6,410,583 B1 | 6/2002 | Labelle et al. |
| 6,413,527 B1 | 7/2002 | Simonnet et al. |
| 6,419,949 B1 | 7/2002 | Gasco |
| 6,423,338 B1 | 7/2002 | Larson et al. |
| 6,433,040 B1 | 8/2002 | Dellamary et al. |
| 6,436,367 B1 | 8/2002 | Modi |
| 6,436,430 B1 | 8/2002 | Mulye |
| 6,440,456 B1 | 8/2002 | Nguyen et al. |
| 6,440,493 B1 | 8/2002 | Gibson et al. |
| 6,444,859 B1 | 9/2002 | Bieniarz et al. |
| 6,451,339 B1 | 9/2002 | Patel et al. |
| 6,464,987 B1 | 10/2002 | Fanara et al. |
| 6,469,069 B1 | 10/2002 | Mirejovsky et al. |
| 6,475,506 B1 | 11/2002 | Inoue et al. |
| 2001/0007663 A1 | 7/2001 | Von Corswant |
| 2001/0008889 A1 | 7/2001 | Caruso et al. |
| 2001/0025035 A1 | 9/2001 | Stella et al. |
| 2001/0041923 A1 | 11/2001 | Dobak, III |
| 2001/0046474 A1 | 11/2001 | Weers et al. |
| 2001/0051595 A1 | 12/2001 | Lyons et al. |
| 2002/0002704 A1 | 1/2002 | Davis et al. |
| 2002/0003179 A1 | 1/2002 | Verhoff et al. |
| 2002/0006442 A1 | 1/2002 | Mishra et al. |
| 2002/0016373 A1 | 2/2002 | Bieniarz et al. |
| 2002/0017296 A1 | 2/2002 | Hickle |
| 2002/0017299 A1 | 2/2002 | Hickle |
| 2002/0017300 A1 | 2/2002 | Hickle et al. |
| 2002/0022667 A1 | 2/2002 | Pace et al. |
| 2002/0025337 A1 | 2/2002 | Illum et al. |
| 2002/0032171 A1 | 3/2002 | Chen et al. |
| 2002/0035141 A1 | 3/2002 | Attala |
| 2002/0035161 A1 | 3/2002 | Segura et al. |
| 2002/0037933 A1 | 3/2002 | Basu et al. |
| 2002/0047058 A1 | 4/2002 | Verhoff et al. |
| 2002/0058009 A1 | 5/2002 | Bartus et al. |
| 2002/0068764 A1 | 6/2002 | Franks et al. |
| 2002/0071852 A1 | 6/2002 | Deckers et al. |
| 2002/0082252 A1 | 6/2002 | Hochman |
| 2002/0102215 A1 | 8/2002 | Klaveness et al. |
| 2002/0102216 A1 | 8/2002 | Lanza et al. |
| 2002/0102217 A1 | 8/2002 | Klaveness et al. |
| 2002/0102281 A1 | 8/2002 | Auberger et al. |
| 2002/0107265 A1 | 8/2002 | Chen et al. |
| 2002/0107291 A1 | 8/2002 | De Tommaso |
| 2002/0115609 A1 | 8/2002 | Onyuksel et al. |
| 2002/0120002 A1 | 8/2002 | Baker et al. |
| 2002/0120015 A1 | 8/2002 | Dennis et al. |
| 2002/0128698 A1 | 9/2002 | Dobak, III et al. |
| 2002/0142093 A1 | 10/2002 | Gibson et al. |
| 2002/0150621 A1 | 10/2002 | Kohane et al. |
| 2002/0160043 A1 | 10/2002 | Coleman |
| 2002/0173547 A1 | 11/2002 | Jones et al. |

FOREIGN PATENT DOCUMENTS

| | | |
|---|---|---|
| DE | 29 38 807 | 11/1980 |
| DE | 3421 468 | 12/1985 |
| EP | 052 322 | 5/1982 |
| EP | 057 829 | 8/1982 |
| EP | 272 091 | 6/1988 |
| EP | 330 532 | 8/1989 |
| EP | 391 369 | 10/1990 |
| EP | 418 153 | 3/1991 |
| EP | 456 670 | 11/1991 |
| EP | 456 764 | 11/1991 |
| EP | 499 299 | 8/1992 |
| EP | 535 567 | 4/1993 |
| EP | 570 829 | 11/1993 |
| EP | 601 618 | 6/1994 |
| EP | 602 700 | 6/1994 |
| EP | 724 877 | 8/1996 |
| EP | 757 911 | 2/1997 |
| EP | 0 770 387 A1 | 5/1997 |
| EP | 770 381 | 5/1997 |
| EP | 770 387 | 5/1997 |
| EP | 814 787 | 1/1998 |
| EP | 1 238 677 | 9/2002 |
| FR | 2 265 357 | 10/1975 |
| FR | 2 617 047 | 12/1988 |
| GB | 2 046 094 | 11/1980 |
| GB | 2 250 197 | 6/1992 |
| GB | 2 298 789 | 9/1996 |
| GB | 2 359 747 | 9/2001 |
| HU | 211 580 | 12/1995 |
| JP | 55-141407 | 11/1980 |
| JP | 56-167616 | 12/1981 |
| JP | 60-208910 | 10/1985 |
| JP | 63-502117 | 8/1988 |
| JP | 63-233915 | 9/1988 |
| JP | 1-502590 | 9/1989 |
| JP | 10-251142 | 9/1998 |
| JP | 2000-119177 | 4/2000 |
| JP | 2002-179562 | 6/2002 |
| WO | WO 85/00011 | 1/1985 |
| WO | WO 87/04592 | 8/1987 |
| WO | WO 91/04011 | 4/1991 |
| WO | WO 93/19736 | 10/1993 |
| WO | WO 94/20072 | 9/1994 |
| WO | WO 96/01637 | 1/1996 |
| WO | WO 96/19064 | 6/1996 |
| WO | WO 96/21439 | 7/1996 |
| WO | WO 96/29064 | 9/1996 |
| WO | WO 96/32135 | 10/1996 |
| WO | WO 97/10814 | 3/1997 |
| WO | WO 97/14407 | 4/1997 |
| WO | WO 98/53805 | 3/1998 |
| WO | WO 98/53805 | 12/1998 |
| WO | WO 99/39696 | 8/1999 |
| WO | WO 00/10531 | 3/2000 |
| WO | WO 00/24376 | 5/2000 |
| WO | WO 00/54588 | 9/2000 |
| WO | WO 00/59471 | 10/2000 |
| WO | WO 00/59472 | 10/2000 |
| WO | WO 00/78301 | 12/2000 |
| WO | WO 01/30372 | 5/2001 |
| WO | WO 02/21517 | 3/2002 |
| WO | WO 02/074200 | 9/2002 |

OTHER PUBLICATIONS

Cox EH et al., "Influence of different fat emulsion . . . " Pharmaceutical Research vol. 15 No. 3, Mar. 1998, pp. 442-448.

"Diprivan 1% injection," Physicians' Desk Reference, 1996, pp. 2833-2839.

"Diprivan 1% Injection," Physicians' Desk Reference, 1999, pp. 3411-3418.

Ardulno, M.J. et al., "Microbial Growth and Endotoxin Production in the Intravenous Anesthetic Propofol", Infection Control and Hospital Epidemiology, vol. 12, No. 9, Sep. 1991, pp. 535-539.

Babl et al., "New Formulations of Propofol in an LCT/MCT Emulsion: Approach to Reduce Pain on Injection", Eur. Hosp. Pharmacy, Jan. 1995, vol. 1, No. 1, pp. 15-21.

Bangham et al., "Diffusion of Univalent Ions Across the Lamellae of Swollen Phospholipids," J. Mol. Biol., 1965, 13:238-251.

Bennett et al., "Postoperative Infections Traced to Contamination of an Intravenous Anesthetic, Propofol", vol. 333, No. 3, Jul. 20, 1995, pp. 147-154.

Benz et al., "Electrical Capacity of Black Lipid Films and of Lipid Bilayers made from Monolayers," Biochimica et Biophysica Acta, 1975, 394:323-334.

Bergmann, Ludwig, Der Ultraschall, 5 Aufl., 1949, Struttgart, pp. 551-564 and 665-677.

Bittman, Robert, "Sterol-Polyene Antibiotic Complexation: Probe of Membrane Structure," LIPIDS, vol. 13, No. 10, pp. 686-691 (1978).

Cairns et al., "Tolerance of Mixed Lipid Emulsion In Neonates: Effect of Concentration", Archives of Disease In Childhood, 1996, vol. 75, p. F113-F116.

Cherney, Leonid S., "Tetracaine Hydroiodide: A Long-Lasting Local Anesthetic Agent for the Relief of Postoperative Pain," Anesthesia and Analgesia, vol. 42, No. 4, Jul.-Aug. 1963, pp. 477-481.

Crowther et al., "Growth of Microorganisms in Propofol, Thiopental and a 1:1 Mixture of Propofol and Thiopental", Anesth. and Anal., (1996), 82, pp. 475-478.

Cudd et al., "Liposomes Injected Intravenously into Mice Associate with Liver Mitochondria," Biochimica et Biophysica Acta, (1984), 774:169-180.

De Sommer et al., "A Comparative Study on the Effects of Propofol in Emulsion and Intralipid® on Fat Metabolism," Acta Anesthesiological Belgica, vol. 41, No. 2, 1990, pp. 133-138.

Dewandre et al., "A Comparison of the 2% and 1% Formulations of Propofol During Anaesthesia for Craniotomy," Anesthesia, 1994, vol. 49, pp. 8-12.

Doenicke, A.W. et al., "Pharmacokinetics and Pharmacodynamics of Propofol in a New Solvent", Anesth. Analg., (1997), 85:1399-403.

Doenicke, A.W. et al., "Reducing Pain During Propofol Injection: The Role of the Solvent", Anesth. Analg., (1996), 82:472-4.

Eddleston et al., "The Effect on Serum Lipid Concentrations of a Prolonged Infusion of Propofol—Hypertriglyceridaemia Associated with Propofol Adminstration," Intensive Care Med., (1991), 17:424-426.

Ewart et al., "Forum: 2% Propofol for Sedatin in the Intensive Care Unit, A Feasibility Study", Anaesthesia, Feb. 1992, vol. 47, No. 2, pp. 146-148.

Freeman, Andrew B., "A Technique for Reducing Pain Associated with Propofol Adminstration," Anesth. Analg., 1992, 74:311-319.

Ghouri et al., "Effect of Flumazenil on Recovery after Midazolam and Propofol Sedation", Anesthesiology, (1994), 81:333-339.

Goodman & Gillman's The Pharmacological Basis of Therapeutics, 7th Ed., MacMillan Publishing Co., New York, 1985. p. 312.

Gottardis et al., Effect of Prolonged Sedation with Propofol on Serum Triglyceride and Cholesterol Concentrations, British J. Anaesthesia, (1989) 62:393-396.

Gregoriadis, Gregory, "The Carrier Potential of Liposomes in Biology and Medicine", The New England Journal of Medicine, Sep. 23, 1976, vol. 295, pp. 704-710.

Haung et al., "Interaction of the N-terminus of Sterol Carrier Protein 2 with Membranes: Role of Membrane Curvature," Biochem. J., (1999), 344:593-603.

Haynes et al. "Ultra-Long Duration Local Anesthesia Produced by Intra-Dermal Injection of Lecithin-Coated Methoxyflurane Microdroplets", Proceed. Intern. Symp. Control. Rel. Bioact. Mater., (1987), 14:293-294 (Extended abstract).

Haynes et al., "Ultra-long-duration Local Anesthesia Produced by Injection of Lecithin-coated Methoxyfluorene Microdroplets", Anesthesiology, Nov. 1985, vol. 63, No. 5, pp. 490-499.

Haynes, Duncan H., "Divalent Cation-Ligand Interactions of Phospholipid Membranes: Equilibria and Kinetics," Metal-Ligand Interactions in Organic Chemistry and Biochemistry, Pullman and Goldblum, Eds., part 2,© 1977, pp. 189-212.

King et al., "Lidocaine for the Prevention of Pain Due to Injection of Propofol," Anesth. Analg., 1992, 74:246-249.

Kirkpatrick et al., "Local Anesthetic Efficacy of Methoxyflurane Microdroplets in Man," Anesthesiology, 1987, 67(3A):A254, Abstract only.

Lindholm, Marianne, "Critically Ill Patients and Fat Emulsions," Minerva Anesthesiology, 1992, vol. 58, No. 10, pp. 875-879.

Mangar et al., "Tourniquet et 50 mm Hg Followed by Intravenous Lidocaine Diminishes Hand Pain Associated with Propofol Injection", Anesth. Analg., (1992), 74:250-252.

Mirakhur et al., "Induction Characteristics of Propofol In Children: Comparison with Thiopenttone", Anesthesia, (1998), 43:593-598.

Mishra et al., "Scientifically Speaking: Novel Injectable Formulations of Water-Insoluble Drugs", Controlled Release Newsletter, vol. 17, Issue 2, Jun. 2000, pp. 21-30.

Nichols, Ronald Lee, "Bacterial Contamination of an Anesthetic Agent," New Engl. J. Med., (1995), 333(3), 184-185.

Rompp, "Emulsion", Chernie-Lexikon, 2 Aufl., Bd. 1, 1950, Stichwort.

Ross, et al., "Aqueous Solutions of Surface-Active Solutes", Colloidal Systems and Interfaces,© 1988, p. 148-151.

Sande et al., "Antimicrobial Agents: Antifungal and Antiviral Agents," p. 1219-1222.

Sandstrom et al., "Structured Triglycerides Were Well Tolerated and Induced Increased Whole Body Fat Oxidation Compared With Long-Chain Triglycerides in Postoperative Patients," Journal of Parenteral and Enteral Nutrition, (1995), 19(5):381-6.

Sklar, Grant E., "Propofol and Postoperative Infections," The Annals of Pharmacotherapy, (1997), 31:1521-3.

Smith et al., "Propofol: An Update on its Clinical Use," Anesthesiology, Oct. 1994, vol. 81, No. 4, pp. 1005-1043.

Sosis et al., "Growth of *Staphylococcus aureus* in Four Intravenous Anesthetics," Anesth. Anal., (1993), vol. 77, pp. 766-768.

Sosis et al., "Propofol, but not Thiopental, Supports the Growth of *Candida albicans*," Anesth. Anal., (1995), vol. 81, pp. 132-134.

Stark, et al., "A review of the safety and tolerance of propofol ('Diprivan')", Postgraduate Medical Journal, 1985, vol. 61, Suppl. 3, pp. 152-156.

Stenz et al., "A new physiologically approached in vitro test for quick evaluation of the hemolytic activity of surfactants," Pharmazie, (1996), 51(5), pp. 283-287.

Tessler et al., "Growth curves of *Staphyloccoccus aureus, Candida albicans*, and *Moraxella osloensis* in propofol and other media", Can. J. Anaesth., 1992, 39 (5), pp. 509-511.

White et al., "Sedative Infusions During Local and Regional Anesthesia: A Comparison of Midazolam and Propofol", J. Clin. Anesth., Jan./Feb. 1991, vol. 3, pp. 32-39.

Wu et al., "Pharmacokinetics of Methoxyflurane after its Intra-dermal Injection as Lecithin-Coated Microparticles", Journal of Controlled Release, 1989, vol. 9, pp. 1-12.

INJECTABLE AQUEOUS DISPERSIONS OF PROPOFOL

This application is a division of application Ser. No. 09/376,487, filed Aug. 18, 1999 and claims benefit of provisional application 60/097,071, filed Aug. 19, 1998.

This invention relates to compositions of propofol (2,6-diisopropylphenol) which have a low lipid content and which can be terminally steam sterilized. These formulations can be used as anesthetic agents in which the potential for microbial growth is either very low or eliminated. The low lipid content of these formulations provides for a low or non-existent risk of incidence of hyperlipidemia. In addition these formulations cause little or no irritation around the site of injection.

BACKGROUND

Prior Art

Propofol formulations have been used as anesthetic agents. Compositions of propofol and their clinical usage have been described in the scientific literature. In a series of patents Glen and James describe compositions containing propofol suitable for parenteral administration to produce anesthesia in warm-blooded animals as described in U.S. Pat. No. 4,056,635 (1977); U.S. Pat. No. 4,452,817 (1984); and U.S. Pat. No. 4,798,846 (1989).

The compositions described by Glen and James in U.S. Pat. Nos. 4,056,635 and 4,452,817 are mixtures of propofol with surfactants such as CREMOPHOR-RH40™or CREMOPHOR-EL™ or TWEEN-80™, in aqueous medium that may also contain ethanol or other pharmaceutically acceptable ingredients.

In a continuation of U.S. Pat. No. 4,452,817 Glen and James describe propofol compositions containing 1% to 2% propofol either alone or dissolved in oil such as arachis oil or ethyl oleate (U.S. Pat. No. 4,798,846). These formulations were claimed to be stabilized with sufficient amount of surfactants selected from polyoxyethylene laurate, stearate, or oleate, a condensation product of ethylene oxide with castor oil, a polyoxyethylene cetyl, lauryl, stearyl or oleyl ether, a polyoxyethylene sorbitan monolaurate, monopalmitate, monostearate, or monooleate, a polyoxethylene-polyoxypropylene block copolymer, a lecithin and a sorbitan monolaurate, monopalmitate, monostearate, or monooleate.

Based on the above patents a propofol preparation for clinical use (PDR 1996) has been commercially available DIPRIVAN 1% Injection) which contains propofol dissolved in soybean oil and is stabilized with egg lecithin. Each milliliter of this formulation consists of 10 mg/mL of propofol, 100 mg/mL of soybean oil, 22.5 mg/mL of glycerol, 12 mg/mL of egg lecithin, sodium hydroxide to adjust pH within 7 to 8.5 and sufficient quantity of water. Although clinically useful, this formulation requires the use of strict aseptic techniques during its handling due to the absence of antimicrobial preservatives and concomitant potential of microorganism growth. Indeed, many incidences of serious infection in human subjects have been linked to the use of the commercially available propofol formulation, DIPRIVAN (Nichols et al. (1995), Tessler et al. (1992), Ardulno et al. (1991), Sosis and Braverman (1993), Sosis et al. (1995), Crowther et al. (1996)).

In order to minimize the chances of infection arising from the handling of the formulations of propofol during intravenous administration Jones and Platt have recently introduced a new propofol formulation, essentially based on the earlier composition with the added component of an antimicrobial preservative. This product is described by U.S. Pat. Nos. 5,714,520; 5,731,355; and 5,731,356. The antimicrobial preservative that is added to the new formulation is disodium edetate. In U.S. Pat. No. 5,714,520 it is claimed that addition of an amount of edetate limits bacterial growth to no more than a 10-fold increase as determined by the growth of each of *Staphylococcus aureus* ATCC 6538, *Escherichia coli* ATCC 8739, *Pseudomonas aeruginosa* ATCC 9027 and *Candida albicans* ATCC 10231 for at least 24 hours as measured by a test wherein a washed suspension of each said organism is added to a separate aliquot of said composition at approximately 50 colony forming units (CFU) per mL, at a temperature in the range 20–25° C., whereafter said aliquots are incubated at 20–25° C. and are tested for viable counts of said organism after 24 hours, said amount of edetate being no more than 0.1% by weight of said composition.

However, regardless of the presence of edetate as a preservative against growth of microorganisms, the product under U.S. Pat. No. 5,714,520 (DIPRIVAN) is not considered an antimicrobially preserved product under USP standards by some authors, for instance, Sklar (1997). While in the quantity that is present, edetate may be effective against the growth of some types of organisms that are claimed in the patent, it may not be so effective against a variety of other organisms that may be prevalent in the clinical situations where propofol is administered such as for example, *C. albicans* ATCC 10231 as noted in U.S. Pat. No. 5,714,520. Indeed, it was noted in patent 5,714,520 that the formulated propofol was not microbicidal against *C. albicans* ATCC 10231 where an approximately 10-fold growth in the inoculum concentration was observed after 48 hours. This result points to the possibility of ineffectiveness of edetate as a preservative against growth of microorganisms in Diprivan® formulation if challenged by other organisms than those cited above or by a higher load of organisms exceeding 100 CFU/mL. Indeed the addition of edetate to the formulation provides little in the way of real improvement. This "improved" formulation continues to be inferior, with respect to antibacterial effectiveness, to the invention described in the Haynes patent (U.S. Pat. No. 5,637,625, see below).

The formulation based on U.S. Pat. Nos. 5,714,520; 5,731,355; and 5,731,356 still consists of a high amount of soybean oil (10%) that has been implicated in causing hyperlipidemia in some patients. Apart from the addition of edetate, this formulation is essentially the same as the previously commercialized Diprivan® formulation. In fact it has the same incidence of adverse effects as the previous product as evidenced by the quoted incidence states for these symptoms in the current PDR, 1999.

Problems in the Clinical Use of Commercial Propofol Formulations

Many authors have reviewed the clinical usage of propofol formulations. For instance, Smith et al. (1994) describe that propofol injection has been used for producing and maintenance of ambulatory anesthesia, neurosurgical and pediatric anesthesia, for monitored anesthesia care, for intensive care sedation, and other clinical situations. Pain after injection of commercial formulations of propofol has been reported to occur in 28–90% of patients e.g., see reports by Mirakhur (1988), Stark et al. (1985), Mangar and Holak (1992). Even with low dose propofol administered for sedation, the incidence of pain can be 33–50%. (White and Negus, 1991; Ghouri et al. 1994). The mechanism responsible for the venous pain upon propofol administration is unknown. The original excipient, CREMOPHOR EL, of the earlier propofol preparation was initially thought to be the causative agent. However, there was no measurable reduction in pain after the change from the CREMOPHOR EL based propofol formulation to the marketed soybean oil and lecithin based formulation (e.g.; see Mirakhur (1988), Stark et al. (1985), Mangar and Holak (1992). White and Negus, 1991; Ghouri et al. 1994). It is believed that the pain is a function of the drug itself, rather than the formulation (Smith et al. (1994)).

To decrease the propensity of pain on injection of propofol formulations, Babl et al. (1995) have reported the use of 1% and 2% propofol preparations with a mixture of medium-chain triglyceride (MCT) and long-chain triglyceride (LCT) in the dispersed oil phase. Similarly, Doenicke et al. (1996, 1997) have demonstrated in human volunteers that use of MCT in the propofol formulation resulted in fewer incidence of severe or moderate pain on injection (9%) compared to that after injection of commercial formulation (59%). These authors have attributed the lower incidence of pain as result of a lower aqueous phase concentration of free propofol that was achieved by increasing the oil concentration in the formulation.

Although increasing the amount of oil may aid in lowering the aqueous propofol concentration and thereby reducing pain on injection, the oil level of as high as 20% used by these authors (Babl et al. 1995, and Doenicke et al. 1996, and 1997) is likely to further compromise patients requiring prolonged administration of propofol in intensive care units, potentially leading to hyperlipidemia.

While pain on injection may or may not be related to the injection-site tissue-irritation or the thrombogenicity of the administered formulation, these adverse reactions are still prevalent and symptoms continue to be reported in the clinical use of propofol. For instance, in the case of DIPRIVAN, these symptoms span the range of thrombosis and phlebitis and include up to 17.6% incidences of burning/stinging or pain (PDR 1999, p. 3416).

Clearly the need still exists for a clinically acceptable propofol formulation that can satisfy the three most often cited shortcomings of currently marketed and previous experimental formulations; viz.,
  a growth of microorganisms,
  excessive lipid content, and
  irritation at the site of injection and/or pain on injection.

Alternative propofol formulations, that addressed some of the above-mentioned clinical problems associated with the commercial (DIPRIVAN) or experimental (e.g., those described by Babl et al. 1995, and Doenicke et al. 1996 and 1997) propofol injectable products, have been taught by Haynes in U.S. Pat. No. 5,637,625. For instance, Haynes has recognized two problems associated with the use of large quantities of vegetable oil in a commercial formulation consisting of 1% propofol and 10% soybean oil:
  (1) hyperlipidemia in patients undergoing long-term sedation in the intensive care unit (ICU), and
  (2) the risk of bacterial contamination secondary to the high lipid content and lack of antimicrobial preservatives.

Haynes described the formulations of phospholipid coated microdroplets of propofol devoid of fats and triglycerides that provide anesthesia and chronic sedation over extended periods of time without fat overload. Prior to Haynes' teachings no oil based propofol formulations were claimed that contained less than 10% (w/w) oil vehicle. Haynes claimed that these microdroplet formulations are bactericidal (e.g. self-sterilizing) because of being free of the material that may support bacterial growth, and thus having extended shelf life.

Considering the observations cited in the clinical literature of propofol, particularly those mentioned above, it appears that Haynes has been able to address two of the three shortcomings, however, there is still a need for a sterile propofol preparation that can be administered as a bolus intravenous injection or could be given as an infusion, e.g., in the ICU and that possesses particularly all of the following characteristics:
  does not have excessive amount of oils or triglyceride in order to reduce the propensity of a patient to fall victim to hyperlipidemia,
  has sufficient bactericidal or bacteriostatic property so as to provide enhanced patient safety and extended shelf life during use in a clinical setting, and
  causes little or no tissue-irritation at the site of injection.

DESCRIPTION OF THE INVENTION

Summary of the Invention

Surprisingly it was found that certain propofol compositions, prepared as an injectable aqueous dispersion of a water-insoluble matrix consisting of propofol and propofol-soluble agents, were capable of substantially limiting or inhibiting the growth of certain microorganisms and did not display the incidence of irritation at the injection site as evidenced by the in-vivo experiments.

It was yet another surprising finding that the property of inhibition of microorganism growth in this formulation did not require the addition of any antimicrobial preservative agents.

Even more surprising was the fact that the said aqueous dispersion of propofol could be prepared as a terminally steam sterilizable and stable product containing various polyhydroxy compounds in its aqueous phase. These polyhydroxy compounds are commonly used in intravenous infusion. It was found that propofol formulations made with the polyhydroxy compounds provided compositions of relatively higher viscosity.

It is also believed that owing to the reduced lipid content, these novel formulations would be much less prone to cause hyperlipidemia in human subjects administered IV formulations of this invention. Additionally, mixtures of LCT and MCT are known to undergo faster metabolic clearance and therefore there use in the propofol formulations of this invention may be clinically advantageous (Cairns et al., 1996; Sandstrom et al., 1995). Accordingly, mixtures of LCT and MCT are one preferred embodiment of the present invention.

Furthermore, the feasibility of formulating very high potency propofol compositions, containing for example 10% w/w propofol, is demonstrated in this invention.

Composition

The novel compositions described in this invention consist of a nanometer to micrometer size water-insoluble matrix containing up to about 15%, or preferably up to 10%, propofol dispersed in an aqueous phase, comprised as follows:

The water-insoluble matrix consists of the anesthetic propofol with lipophilic agents dissolved to adjust the level of anti-microbial activity and the degree of local reaction on injection. Examples of such lipophilic agents include but are not limited to either one or more selected from saturated or unsaturated fatty acid esters such as isopropyl myristate, cholesteryl oleate, ethyl oleate, squalene, squalane, alpha-tocopherol and/or derivatives of alpha-tocopherol, esters or triglycerides of either medium chain and/or long chain fatty acids of synthetic or natural origin. The natural triglycerides can be selected particularly from the vegetable or animal sources, e.g., pharmaceutically acceptable vegetable oils or fish oils. The latter are also known as omega-3 polyunsaturated oils. The lipophilic agents may also be considered propofol-soluble agents or diluents.

At the surface of the water-insoluble matrix are amphiphilic agents that stabilize the dispersion and are of possible importance in affecting the degree of local reaction on injection. Examples of such amphiphilic agents include charged or uncharged phospholipids of natural sources, e.g., egg or soy lecithin, or hydrogenated lecithin (e.g., PHOSPHOLIPON-90H™ or PHOSPHOLIPON-100H™ from Nattermann), or synthetic phospholipids such as phosphatidylcholines or phosphatidylglycerols, pharmaceutically acceptable non-ionic surfactants such as poloxamers PLURONIC series of surfactants), poloxamines (TETRONIC series of surfactants), polyoxyethylene sorbitan esters (e.g., TWEEN™ series of surfactants), cholesterol, or other surface modifiers commonly used in pharmaceutical products, or combinations of these surface modifiers.

The aqueous phase consists substantially of a mixture of pharmaceutically acceptable polyhydroxy tonicity modifiers such as those commonly used in intravenous infusions, for example sucrose, dextrose, trehalose, mannitol, lactose, glycerol, etc. Preferably, the polyhydroxy compounds are in a quantity sufficient to render the final composition isotonic with blood or suitable for intravenous injection. In case the amount of these polyhydroxy compounds in the formulation is selected such that it is not isotonic with blood, it can be diluted with suitable diluent prior to injection to adjust the tonicity. The aqueous phase may additionally contain some amount of pH adjusting agents such as sodium hydroxide and/or pharmaceutically acceptable acids and/or related salts thereof. Preferably, the pH is adjusted to be between about 9 to about 4, and more preferably between about 8 to 5. Pharmaceutically acceptable buffer systems may be utilised.

The compositions of the invention may optionally contain other pharmaceutically acceptable agents, for example other antimicrobial agents, local or long acting anesthetics, chelating agents or antioxidants. Examples of which include but are not limited to parabens or sulfite or edetate, lidocaine, or metabisulfite.

Preferably, the compositions of the invention are selected so as to be stable to terminal sterilization under pharmaceutically acceptable conditions.

It was found that propofol formulations made with the polyhydroxy compounds provided compositions of relatively high viscosity. The viscosity of these preparations is from about 1.5 to 8 centipoises and more preferably from about 4 to 6 centipoises. While not adhering to any particular theory, it is believed that such high viscosities may be partly responsible for minimizing the tissue-irritating effect of the formulation.

Method

Propofol is a liquid that is very poorly soluble in water. To manufacture stable injectable propofol formulations with the desired anti-microbial properties, low lipid content and low injection site reactivity and with little or no phase separation of the propofol during mixing or storage, it was found necessary to not only select an appropriate composition of the formulation but also use appropriate processing conditions. Examples of suitable processing conditions are those which provide intense mechanical agitation or high sheer, see for example the procedures described by Haynes (U.S. Pat. No. 5,637,625). The formulation is conveniently prepared by the initial preparation of a lipophilic phase and an aqueous phase which are then mixed. However, those skilled in the art will appreciate that alternate approaches may be suitable and will readily be able to determine such approaches. For example, the unit processes as described briefly in the following paragraphs have proven suitable.

Premix Preparation

Propofol, other lipophilic agents, and ampiphilic agents were mixed to prepare the lipophilic phase. The dissolution process was accelerated by heating the mixture while mixing with a high-speed homogenizer. The aqueous phase was usually a mixture of polyhydroxy compounds in water and in some cases also contained well-dispersed phospholipid prepared using a high-speed homogenizer. The premix was prepared by adding the lipophilic phase to the aqueous phase under agitation with a high-speed homogenizer and the pH adjusted. All these operations were performed under a generally inert atmosphere, for example a nitrogen blanket, and the temperature was controlled to minimize oxidation.

Homogenization

The dispersions of the water insoluble matrix in aqueous medium were prepared by either of several homogenization methods. For example, dispersions were prepared by high pressure homogenization of the premix e.g., by utilizing a Rannie MINI-LAB, type 8.30H Homogenizer, APV Homogenizer Division, St. Paul, Minn. Alternatively, the dispersions were made by microfluidization of the premix with a Microfluidizer M110EH (Microfluidics, Newton, Mass.). The temperature of the process-fluid rises rapidly because of homogenization at a high pressure. In some cases high-pressure homogenization at high temperatures (homogenizer inlet temperature above about 30° C.) resulted in a dispersion with a tendency to suffer from phase separation. Therefore, the effluent of the homogenizer was cooled to maintain an acceptable temperature at the inlet of the homogenizer.

Packaging and Sterilization

The aqueous dispersion prepared by one of the above processes was filled into glass vials to about 70–90% volume capacity, purged with a generally inert atmosphere, for example nitrogen, and sealed with compatible stoppers and seals. The packaged novel propofol formulations were found generally to be stable pharmaceutically acceptable steam sterilization cycles.

Rat Tail Vein Irritation Experiments

The propofol formulations prepared using the method described above were tested for their ability to cause irritation to the venous tissues by intravenous injection to rats. Female Sprague-Dawley rats, approximately 11 to 12 weeks of age were purchased from Charles River, St. Constant, PQ. Following an acclimation period, rats that appeared healthy, and weighing between 200 and 250 grams, were used.

The formulation to be tested was administered as a single daily bolus injection for 2 days, i.e., on Day 1 and Day 2.

The injections were made over a period of approximately 30 seconds, in the caudal vein at a site located approximately 5 cm from the distal end of the tail. The propofol dose of 12.5 mg/kg was given on the basis of body weights determined on Day 1. Rats were observed daily on study Day 1 through Day 3 as follows.

I. General Observation

The animals were checked for general health/mortality and morbidity once daily for three consecutive days. Detailed clinical observations were recorded daily. The animals were observed for overt toxic effects following the intravenous dosing.

II. Tail Vein Irritation

The circumference of the rat's tail was measured at approximately 2.5 inches proximal to the animal's body prior to the administration of the test formulation. This measurement served as a baseline value for assessing possible swelling of the tail upon intravenous administration of the formulation. On each study day, the treatment site was carefully examined to detect any reactions and the rat's tail circumference measured. Changes in the rat's tail circumference were evaluated by comparing Day 2 and Day 3 measurement to the baseline value obtained before administering the test articles.

Pharmacodynamic Indicators

Each rat of the above experiment was observed during and after the injection. The time required for loss of consciousness (induction time) was recorded. The time to recover (righting response time), indicated by spontaneous attempts to stand up on four feet was also measured. The duration of anesthesia was measured as the difference between the time when righting response occurred minus the time when consciousness was lost.

Hemolysis Potential

In-vitro evaluation of the hemolytic influence of the preparations of this invention on human whole-blood was determined as a further guide to selecting formulations with a low tendency to produce irritation around the site of injection. The hemolytic potential of the formulation on blood was evaluated by the assay of erythrocyte cytoplasmic marker enzyme, lactate dehydrogenase (LDH). Measurement of erythrocyte cytoplasmic marker enzyme. LDH, which escapes from the leaky or ruptured erythrocytes into tie plasma compartment of the blood, is one of the commonly used quantitative assays described in literature for evaluation of hemolytic potential of injectable formulations (Stenz and Bauer, 1996). The blood was obtained from male or female Caucasian human volunteers of 18 to 65 years age and stabilized with sodium heparin. The test formulation was mixed with an equal volume of human whole blood and incubated at 37° C. for about 1 hour. The mixture was then held at ambient temperature for 30 min. followed by centrifugation at 1500 rpm for 10 min. The level of LDH in the supernatant was determined by a standard procedure known to the scientists skilled in this art. As a guide for the present study, a preferred upper limit of acceptability was determined by measuring the LDH levels resulting from applying the hemolysis potential methodology to amiodarone hydrochloride, a compound known to result in vein imitation upon venous injection in clinical settings (PDR 1999, p. 3289). Amiodarone hydrochloride IV solution, tested at 50 mg/mL and after dilution with 5% aqueous dextrose to 1.8 mg/mL as instructed in the product monograph, resulted in LDH values of 8190 IU/L and 673 IU/L respectively.

Inhibition of Microorganisms

The formulations described in the present inventions were tested for their ability to inhibit the growth of microorganisms that are a potential source of most likely infections in the clinical situation. Growth of Staphylococcus aureus (ATCC 6538), Eseherichia coli (ATCC 8739 and ATCC 8454), Pseudomonas aeruginosa (ATCC 9027), Candida albicans (ATCC 10231), and Aspergillus niger (ATCC 16403) was measured by a test wherein a washed suspension of each said organism is added to a separate aliquot of a formulation at approximately 1000 colony forming units (CFU) per mL, at a temperature in the range 20–25° C. The inoculated mixtures are incubated at 20–25° C. The viability of the microorganisms in the inoculated formulation is determined by counting the colonies of said organism after 24 and 48 hours, 7 days and other suitable lengths of time.

EXAMPLES

Examples of various formulations including those according to the invention are briefly summarized in the following examples. The in-vivo or in-vitro behavior of some specific compositions are also presented in these examples.

Unless otherwise specified, all parts and percentages reported herein are weight per unit weight (w/w), in which the weight in the denominator represents the total weight of the formulation. Diameters of dimensions are given in millimeters (mm=$10^{-3}$ meters), micrometers ($\mu$m=$10^{-6}$ meters), or nanometers (nm=$10^{-9}$ meters). Volumes are given in liters (L), milliliters (mL=$10^{-3}$ L), and microliters ($\mu$L=$10^{-6}$ L). Dilutions are by volume. All temperatures are reported in degrees Celsius. The compositions of the invention can comprise, consist essentially of, or consist of the materials set forth and the process or method can comprise, consist essentially of, or consist of the steps set forth with such materials.

The invention is further explained with reference to the following preferred embodiments and the undesirable compositions are also noted. The general procedure used for the examples have been mentioned above; exceptions are noted. The formulations were prepared by the method mentioned above. The raw materials used to prepare the formulations of this invention are summarized below:

| Raw Material | Symbol | Source |
| --- | --- | --- |
| 1,2-Dimyristoyl-sn-Glycero-3-Phosphocholine | DMPC | Avanti Polar Lipids Inc., Alabaster, AL, US |
| 1,2-Dimyristoyl-sn-Glycero-3-[Phospho-rac-(1-glycerol)] | DMPG | Avanti Polar Lipids Inc., Alabaster, AL, US |
| Ethyl Oleate, NF | EO | Croda Leek Ltd, Staffordshire, UK |

-continued

| Raw Material | Symbol | Source |
|---|---|---|
| Glycerin, USP-FCC | GLY | J. T. Baker, Philipsburg, NJ, US |
| Lipoid E80 ™ (egg lecithin) | E80 | Lipoid GmBH, Ludwigshafen |
| Lipoid EPC ™ (egg phosphatidylcholine) | EPC | Lipoid GmBH, Ludwigshafen |
| Lipoid SPC ™ (soy phosphatidylcholine) | SPC | Lipoid GmBH, Ludwigshafen |
| Lipoid SPC-3 (saturated soy phosphatidylcholine) | SSPC | Lipoid GmBH, Ludwigshafen |
| Mannitol, USP | MAN | J. T. Baker, Philipsburg, NJ, US |
| Miglyol 810 ™ | M810 | Hüls America, Piscatway, NJ, US |
| Propofol | PRO | Albemarle Corporation, Baton Rouge, LA, US |
| Soybean oil, USP | SO | Spectrum, New Brunswick, NJ, US |
| (D+)Alpha, alpha-Trehalose | TRE | Pfanstiehl Laboratories Inc, Waukegan, IL, US |

Example 1

Effect of Increasing Oil Content of the Formulation

Experiments of this example were performed to identify the formulation variables that are factors behind the desirable attributes.

Table I summarizes some examples of the propofol formulations and their attributes with increasing amount of oil. The oil concentration of these formulations was increased by increasing the amount of ethyl oleate from 0.4% to 10%. Propofol concentration was kept at 1%. Amount of the phospholipid mixture (LIPOID E80 and DMPG) was adjusted with increasing amount of oil to obtain the formulations of good stability.

Rat-tail swelling, an indicator of the tissue-irritation propensity of the formulation (see above), was found to decrease with increasing amount of oil. Formulation #1.4–1.6 with 4–10% ethyl oleate appear to result in unnoticeable rat-tail swelling. This result parallels the reported finding (Babl et al. 1995, and Doenicke et al. 1996, and 1997) that the use of higher amounts of oil in propofol preparations reduces the incidence of pain on injection possibly by a reduction of aqueous concentration of propofol. However, these authors have used a much higher amount (20%) of MCT and LCT mixture in their propofol formulations, and such formulations are expected to support the growth of microorganisms.

TABLE I

Effect of increasing oil content of the formulation

| Formulation ID | Propofol (%, w/w) | LIPOID E80 (%, w/w) | DMPG (%, w/w) | Ethyl Oleate (%, w/w) | Viscosity, cP | Rat Tail Swelling, at 48 hr, mm | LDH (IU/L) |
|---|---|---|---|---|---|---|---|
| 1.1 | 1 | 0.8 | 0.15 | 0.4 | 0.97 | 1.39 | 10918 |
| 1.2 | 1 | 0.8 | 0.10 | 1.0 | 1.08 | 0.6 | 10970 |
| 1.3 | 1 | 0.8 | 0.10 | 2.0 | 1.06 | 0.2 | 10300 |
| 1.4 | 1 | 1.0 | 0.25 | 4.0 | 1.04 | 0 | 3150 |
| 1.5 | 1 | 1.0 | 0.25 | 8.0 | 1.25 | 0 | 1290 |
| 1.6 | 1 | 1.0 | 0.25 | 10.0 | 1.34 | 0 | 770 |

Hemolytic potential of the formulations of Table I was evaluated as mentioned above, by measuring LDH activity in a sample of human blood mixed with an equivalent amount of the formulation. The results summarized in Table I demonstrate that the hemolytic potential of the formulation decreases with increasing amount of ethyl oleate.

Although formulation #1.6 with 10% ethyl oleate may possess tolerable hemolytic and injection-site tissue-irritation potential, this formulation is far from satisfactory for the purpose of this invention as it contains a high amount of oil, i.e., ethyl oleate. The problems associated with currently marketed or experimental propofol formulations have been mentioned in the prior art. It has been recognized that a desirable propofol formulation for bolus intravenous injection or for infusion should possess all of the following characteristics simultaneously:

the formulation does not have excessive amount of oils or triglyceride in order to reduce the propensity of a patient to fall victim to hyperlipidemia, the formulation causes little or no irritation at the site of injection, and has sufficient bactericidal or bacteriostatic property to provide enhanced patient safety and extended shelf life during use in a clinical setting.

Thus a better suited formulation will have an acceptable level of injection-site tissue-irritation potential but with much lower oil content than in the best formulation (#1.6) of this example. Many such formulations that fulfill these criteria are described in the following examples.

Example 2

Rat-Tail Vein Irritation and Hemolytic Potential

In this example are shown a number of formulations that were prepared according to the procedure mentioned above and demonstrate acceptable injection-site tissue-irritation as assessed by the rat-tail vein swelling experiments (see above). These formulations are summarized in Table II. A non-existent irritation potential is displayed by zero increase in the tail circumference upon caudal vein intravenous administration to rats, e.g. of formulation numbers 2.1 to 2.25.

Nevertheless, there were a number of compositions that caused an observable irritation of the tail vein, e.g., formulation numbers 2.26 to 2.29 as well as formulation 2.30 which is reproduced here as described by the Haynes patent (U.S. Pat. No. 5,637,625).

In Example 1 it was observed that by increasing the amount of oil from 0.4% to 10% or greater in the formulation, the tissue-irritation potential could be decreased. However, Example 2 indicates that this simplistic notion is not without limitation since in some cases merely increasing the amount of oil in the propofol formulation does not result in a less irritating formula. For instance, in formulation 2.26 the oil level is increased to 6% of ethyl oleate and in formulations 2.27 and 2.28 to 4% of MIGLYOL 810, but these formulations are still injection-site tissue-irritating, which is evident from the tail swelling values for these formulations.

While the formulations of 2.26–2.30 were irritating, it was surprising that many compositions containing oil level of only up to 4% were non-irritating. For instance, formulation 2.15, which contained as low as only 2% oil, was also a non-irritating preparation. This unexpected result indicates that the preferred compositions of these formulations are not self evident from traditional formulation approaches using linear factorial experimental design not able to reveal possible synergistic effects. Once having identified an acceptable range for the compositional elements of the formulations which demonstrate acceptable properties, the selection of preferred embodiments is a matter of routine determination using the approaches described above.

An inspection of the data in Table II leads to a surprising finding that many of the compositions which had an acceptable low LDH level while maintaining no evidence of injection-site tissue-irritation, also had either mannitol or trehalose in their aqueous phase. It was further surprising that the viscosity of many of these compositions was greater than 1.2 centipoise and in many cases even greater than 3 centipoise. A high viscosity of these formulations may possibly render them safer with respect to their hemolytic potential.

As established in Example 1 and again here in Example 2, merely increasing the oil level in formulations did not result in decreasing the hemolytic potential, or irritation to the tissues at the site of injection. It appears that below a certain amount of oil (e.g., <10%) the causative factors for improving the hemolytic potential or tissue irritation is a combination of various factors that originate from the specific composition. Thus, the non-irritating formulations that also have a low potential of hemolysis are characterized by various formulation components that provide the co-operative effects rendering the preferred formulations less irritating.

Example 3

Inhibition of Microorganisms

Whether the formulations demonstrated the absence of thrombogenic irritation in rats or caused such irritation, all were examined for the microbicidal or microbistatic effectiveness as mentioned above of which some relevant results are summarized in Table III. Also presented in Table III are the microbicidal effectiveness test results for DIPRIVAN as a comparison.

There are many compositions that were found to inhibit the growth of microorganisms. Inhibition of microbial growth was determined by a reduction or maintenance in the number of colonies of the inoculated microorganisms. As examples, formulation numbers 2.1, 2.3, and 2.4 of Table II display all the required properties in concert; reduction in irritation potential (no swelling of the rat-tail vein), acceptable hemolytic potential (low LDH values) as well as inhibition of growth of the tested microorganisms (see Table III).

TABLE II

Compositions of some propofol formulations, rat tail vein irritation by these formulations and the hemolytic potential as measured by the lactate dehydrogenase (LDH) levels on incubating with human blood.

| Formulation Number | Propofol | Phospholipids | | | | | | | Oil | | | Tonifier | | Attributes | | |
| | | E80 | EPL | EPC | SPC | SSPC | DMPC | DMPG | EO | SO | M810 | Type | Qty | Tail Swelling at 48 hr, mm | LDH (IU/L) | Viscosity, cP |
| --- | --- | --- | --- | --- | --- | --- | --- | --- | --- | --- | --- | --- | --- | --- | --- | --- |
| 2.1 | 2 | | | | 2.0 | 0.5 | | 0.05 | | | 4 | MAN | 5.5 | 0 | 179 | 5.31 |
| 2.2 | 2 | | | | 2.2 | | | 0.15 | | 4 | | MAN | 5.5 | 0 | 287 | 4.44 |
| 2.3 | 2 | | | | 2.0 | 0.5 | | 0.05 | | | 4 | MAN | 5.5 | 0 | 107 | 5.24 |
| 2.4 | 2 | | 1.6 | | | | | 0.10 | | | 6 | TRE | 12.5 | 0 | 172 | 4.20 |
| 2.5 | 2 | | 1.6 | | | | | 0.05 | | | 4 | MAN | 5.5 | 0 | 183 | 1.32 |
| 2.6 | 2 | | 1.6 | | | | | | | | 4 | MAN | 5.5 | 0 | 168 | 1.21 |
| 2.7 | 2 | 3.0 | | | | | | 0.15 | 4 | | | TRE | 20.0 | 0 | 185 | 1.91 |
| 2.8 | 2 | | | | 2.0 | 0.5 | | 0.05 | | 4 | | MAN | 5.5 | 0 | 204 | 3.64 |
| 2.9 | 2 | 2.4 | | | | | | 0.15 | | 4 | | MAN | 7.5 | 0 | 380 | 1.39 |
| 2.10 | 2 | 2.0 | | | | | | 0.10 | | | 4 | GLY | 2.5 | 0 | 571 | 1.32 |
| 2.11 | 2 | | 1.6 | | | | | | 4 | | | MAN | 7.5 | 0 | 604 | 1.21 |
| 2.12 | 2 | 1.6 | | | | | | 0.15 | | | 4 | GLY | 2.5 | 0 | 668 | 1.20 |
| 2.13 | 2 | 1.6 | | | | | | | 4 | | | MAN | 7.5 | 0 | 942 | 1.20 |
| 2.14 | 1 | 1.0 | | | | | | 0.25 | 8 | | | GLY | 2.5 | 0 | 1290 | 1.25 |
| 2.15 | 1 | | | | | 0.80 | | 0.10 | | | 2 | GLY | 2.5 | 0 | 2049 | 1.18 |
| 2.16 | 2 | | 1.6 | | | | | | | | 4 | GLY | 2.5 | 0 | 2197 | 1.08 |
| 2.17 | 2 | | 1.6 | | | | | 0.10 | 6 | | | GLY | 2.5 | 0 | 2700 | 1.23 |
| 2.18 | 2 | 1.6 | | 1.6 | | | | 0.05 | 4 | | | GLY | 2.5 | 0 | 2826 | 1.17 |
| 2.19 | 2 | | 1.6 | | | | | 0.05 | | | 4 | GLY | 2.5 | 0 | 3650 | 1.17 |
| 2.20 | 2 | 1.6 | | | | | | 0.10 | | 4 | | GLY | 2.5 | 0 | 5035 | 1.13 |
| 2.21 | 2 | 1.6 | | | | | | 0.10 | 6 | | | GLY | 2.5 | 0 | 7565 | 1.33 |
| 2.22 | 1 | | | | | 1.0 | | 0.10 | | | 6 | GLY | 2.5 | 0 | 7720 | 1.45 |
| 2.23 | 1 | | | | | 1.5 | | 0.10 | | | 10 | GLY | 2.5 | 0 | 7940 | 2.78 |
| 2.24 | 2 | 1.6 | | | | | | 0.10 | 4 | | | GLY | 2.5 | 0 | 8250 | 1.15 |
| 2.25 | 1 | | | | | 2.0 | | 0.10 | | | 8 | GLY | 2.5 | 0 | 8710 | 2.25 |
| 2.26 | 1 | 1.0 | | | | | | 0.25 | 6 | | | GLY | 2.5 | 0.2 | 7020 | 1.12 |
| 2.27 | 1 | | | | | | 1.00 | 0.10 | | | 4 | GLY | 2.5 | 0.2 | 7460 | 1.49 |

TABLE II-continued

Compositions of some propofol formulations, rat tail vein irritation by these formulations and the hemolytic potential as measured by the lactate dehydrogenase (LDH) levels on incubating with human blood.

| Formulation Number | Propofol | Phospholipids | | | | | | | Oil | | | Tonifier | | Attributes | | |
|---|---|---|---|---|---|---|---|---|---|---|---|---|---|---|---|---|
| | | E80 | EPL | EPC | SPC | SSPC | DMPC | DMPG | EO | SO | M810 | Type | Qty | Tail Swelling at 48 hr, mm | LDH (IU/L) | Viscosity, cP |
| 2.28 | 2 | | 1.6 | 1.6 | | | | 0.05 | | 4 | | GLY | 2.5 | 0.4 | 4330 | 1.53 |
| 2.29 | 2 | 1.6 | | | | | | 0.10 | | 2 | | GLY | 2.5 | 1.05 | 8765 | 1.01 |
| 2.30 | 1 | 0.8 | | | | | | 0.15 | 0.4 | | | GLY | 2.5 | 0.8 | 10720 | 0.95 |

Symbols and Note:
DMPC: dimyristoylphosphatidylcholine; DMPG: dimyristoylphosphatidylglycerol; E80: LIPOID E80; EO: ethyl oleate; EPC: egg phosphatidylcholine; EPL: egg phospholipids; GLY: Glycerin; M810: MIGLYOL 810; MAN = Mannitol; SO: soybean oil; SPC: soy phosphatidylcholine; SSPC: saturated soy phosphatidylcholine; TRE = Trehalose. Sources of these raw materials are mentioned above.

TABLE III

Log growth of certain microorganisms following an intial inoculation of $10^3$ CFU/ml, in presence of some propofol formulations.

| Formulation ID of Example 2 | Formulation | Organism | | | | | | | | | | | | | | |
|---|---|---|---|---|---|---|---|---|---|---|---|---|---|---|---|---|
| | | C. albicans ATCC 10231 | | | P. aeruginosa ATCC 9027 | | | E. coli ATCC 8739 | | | A. niger ATCC 16403 | | | S. aureus ATCC 6538 | | |
| | | Plating Time | | | | | | | | | | | | | | |
| | | 24 hr | 48 hr | 7 day | 24 hr | 48 hr | 7 day | 24 hr | 48 hr | 7 day | 24 hr | 48 hr | 7 day | 24 hr | 48 hr | 7 day |
| 2.1 | 91.103 | 2.8 | 2.7 | 2.1 | 1.5 | 1.0 | 1.0 | 1.7 | 1.6 | 1.0 | 2.8 | 2.8 | 2.7 | 2.4 | 1.0 | 1.0 |
| 2.3 | 61.103 | 2.8 | 2.3 | 1.3 | 1.0 | 1.0 | 1.0 | 1.0 | 1.0 | 1.0 | 2.0 | 2.1 | 2.0 | 1.0 | 1.0 | 1.0 |
| 2.4 | 76.103 | 2.7 | 2.7 | 2.5 | 2.3 | 1.3 | 1.0 | 2.5 | 2.1 | 1.0 | 2.9 | 2.8 | 2.7 | 2.2 | 1.0 | 1.0 |
| 2.5 | 81.103 | 3.0 | 3.9 | 6.0 | 2.4 | 6.0 | 6.8 | 4.8 | 6.8 | 6.8 | 2.8 | 2.6 | 2.5 | 3.3 | 3.2 | 1.3 |
| 2.6 | 80.103 | 2.9 | 3.4 | 5.8 | 1.0 | 1.0 | 1.0 | 4.4 | 6.8 | 6.8 | 2.8 | 2.6 | 2.6 | 3.0 | 2.5 | 1.0 |
| 2.11 | 72.103 | 3.1 | 4.0 | 5.8 | 2.3 | 5.9 | 6.8 | 5.1 | 6.8 | 6.8 | 2.9 | 2.7 | 2.6 | 3.2 | 3.1 | 1.0 |
| 2.13 | 50.103-A | 4.2 | 5.0 | 5.3 | 2.0 | 3.7 | 6.8 | 1.0 | 1.0 | 1.0 | 2.5 | 2.4 | 2.1 | 2.0 | 1.0 | 1.0 |
| | DIPRIVAN | 3.2 | 3.4 | 3.2 | 2.8 | 3.3 | 6.2 | 2.2 | 1.0 | 1.0 | 2.9 | 2.7 | 2.6 | 3.2 | 3.1 | 1.8 |

It was surprising to note that these compositions also had either mannitol or trehalose in their aqueous phase. It was further surprising that the viscosity of these compositions was as high as from about 4.2 to about 5.3 centipoise.

As taught by Haynes (U.S. Pat. No. 5,637,625) it may be thought that increasing the amount of lipidic nutrients in the formulation would cause the formulation to support microorganism growth. However, it is surprising to note that by increasing the amount of oil (to up to 4–6%), formulations 2.1, 2.3 or 2.4 do not provide a medium for bacterial growth. It is worth noting that formulations 2.1, 2.3, and 2.4 were neither irritating, nor hemolytic while also inhibiting the growth of microorganisms. These non-irritating, non-hemolytic, and bactericidal or bacteristatic formulations are characterized as non-limiting examples of preferred compositions of this invention.

Example 4

High Potency Propofol Formulations

High potency propofol formulations, 4.1–4.3 in Table IV, were prepared by the methods described above. These formulations were found to be terminally steam sterilizable without destabilization.

TABLE IV

Propofol formulations of high drug potency

| | Formula 4.1 | Formula 4.2 | Formula 4.3 |
|---|---|---|---|
| Propofol | 5.0% | 10.0% | 10.0% |
| Cholesterol | 0.25% | 0.4% | 0.5% |
| Cholesteryl oleate | — | 4.0% | 3.0% |
| PHOSPHOLIPON 90H | 1.5% | 1.8% | 1.5% |
| DMPG | 0.3% | 0.3% | 0.15% |
| Glycerol | 2.5% | 2.5% | 2.5% |
| Sodium hydroxide | qs pH 6.9 | qs pH 8.2 | qs pH 7.0 |
| Water | qs 100% | qs 100% | qs 100% |

These high-potency formulations have been found to be very stable and use pharmaceutically acceptable ingredients without altering the efficacy of the drug. For instance, upon intravenous administration to rats of a dose at 10 mg/kg, formulation 4.1 demonstrated acceptable efficacy of general anesthesia.

The formulation 4.2 demonstrates a homogeneous propofol dispersion in aqueous vehicle of 2.5% glycerol. It has as high as 10% propofol, while maintaining a very low fat (cholesterol and cholesteryl oleate) content. It has a volume weighted mean particle size of 82 nm that did not change significantly upon being subjected to various stresses such as freeze/thaw, (128 nm after 3 cycles).

The formula 4.3 is also a very homogeneous dispersion in aqueous vehicle of 2.5% glycerol and consists of 10% propofol while maintaining a very low fat content. It has a volume weighted mean particle size of 80 nm that did not change significantly upon storage at 25° C. (71 nm after 70 days).

The high potency formulation (e.g., 10% propofol) would be useful in achieving a much lower volume for intravenous administration while giving the same effective dose. Therefore, the formulations described in this example will allow a relatively smaller contact area of the blood vessel wall with the formulation and may be important with respect to minimizing the incidences of pain or other local adverse reaction on injection.

Such high potency stable formulations of propofol have been prepared and described here for the first time.

Example 5

Pharmacodynamics

Propofol formulations of this invention were compared for induction and duration of anesthesia in rats with the reference commercial formulation, DIPRIVAN (1%) and DISOPRIVAN (2%). Following 12.5 mg/kg single bolus intravenous injection of these formulations in rats, the time for loss of consciousness and righting response time were measured as mentioned above in the experimental method section. The results are summarized in Table V illustrating the efficacious characteristic, of these formulations.

TABLE V

Pharmacodynamic Parameters

| Formulation ID | Number of Rats | Average Anesthesia Induction Time (sec) | Average Righting Response Time (min) |
|---|---|---|---|
| 2.1 | 9 | 24.4 | 14.9 |
| 2.2 | 4 | 31.0 | 16.2 |
| 2.3 | 4 | 48.0 | 16.4 |
| 2.4 | 9 | 32.7 | 15.8 |
| 2.5 | 9 | 27.2 | 19.2 |
| 2.6 | 9 | 38.4 | 19.4 |
| 2.7 | 4 | 24.0 | 17.3 |
| 2.8 | 4 | 23.8 | 16.7 |
| 2.9 | 3 | 67.3 | 11.9 |
| 2.10 | 4 | 34.8 | 16.3 |
| 2.11 | 8 | 40.5 | 18.6 |
| 2.12 | 4 | 36.3 | 13.7 |
| DIPRIVAN (1% with EDTA) | 4 | 20.0 | 14.6 |

According to the examples given above, the present invention provides for the identification of propofol formulations that are:

(a) stable during and after steam sterilization,
(b) give the required anesthetic effect upon intravenous injection to warm blooded animals,
(c) inhibit the growth of microorganisms,
(d) have demonstrated minimum or non-existent incidences of local vein reaction, and
(e) have a potential of minimum or non-existent incidence of hyperlipidemia.

While the invention and the examples have been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the following claims.

REFERENCES

Ardulno, M. J., Bland, L. A., McAllister, S. K., Aguero, S. M., Villarino, M. E., McNeil, M. M., Jarvis, W. R. and Favero, M. S. (1991) "Microbial Growth and Endotoxin Production in the Intravenous Anesthetic Propofol" Inf. Control Hosp. Epidem., 12(9), 535–539.

J. Babl, A. Doenicke, V. Monch (1995) "New propofol LCT/MCT fat emulsions as solvent. Approach to reducing pain on injection of propofol." Eur Hosp Pharmacy, 1: 15–21.

Cairns et al. (1996) "Tolerance of mixed lipid emulsion in neonates: effect of concentration." Arch Dis Child Fetal Neonatal Ed 75(2): F113–6.

Crowther, J., Hrazdil, J., Jolly, D. T., Galbraith, J. C., Greacen, M. and Grace, M. (1996) "Growth of Microorganisms in Propofol, Thiopental and a 1:1 Mixture of Propofol and Thiopental" Anesth. and Anal. 82, 475–478.

A. W. Doenicke, J. Babl, W. Kellermann, J. Rau, M. F. Roizen (1996) "Reducing pain during propofol injection: the role of the solvent." Anesth Analg 82: 472–4.

A. W. Doenicke, J. Babl, U. Klotz, J. Kugler, M. O'Connor, J. Rau, M. F. Roizen (1997) "Pharmacokinetics and pharmacodynamics of propofol in a new solvent." Anesth Analg 85: 1399–403.

A. F. Ghouri, M. A. Ramirez Ruiz, and P. F. White (1994) "Effect of flumazenil on recovery after midazolam and propofol sedation." Anesthesiology 81: 333–339.

J. B. Glen and R. James "2,6-Diisopropylphenol as an anaesthetic agent." U.S. Pat. No. 4,056,635. Nov. 1, 1977

J. B. Glen and R. James "Anaesthetic compositions containing 2,6-diisopropylphenol." U.S. Pat. No. 4,452,817. Jun. 5, 1984

J. B. Glen and R. James "Pharmaceutical compositions." U.S. Pat. No. 4,798,846. Jan. 17, 1989

D. H. Haynes "Propofol microdroplet formulations." U.S. Pat. No. 5,637,625. Jun. 10, 1997.

C. B. Jones and J. H. Platt "Propofol compostion containing edetate." U.S. Pat. No. 5,714,520. Feb. 3, 1998.

C. B. Jones and J. H. Platt "Pharmaceutical compositions of propofol and edetate." U.S. Pat. No. 5,731,355. Mar. 24, 1998.

C. B. Jones and J. H. Platt "Pharmaceutical compositions of propofol and edetate." U.S. Pat. No. 5,731,356. Mar. 24, 1998.

D. Mangar and E. J. Holak (1992) "Tourniquet at 50 mm Hg followed by intravenous lidocain diminishes hand pain associated with propofol injection." Anesth Analg 74: 250–252.

R. K. Mirakhur (1988) "Induction characteristics of propofol in children: Comparison with thiopentone." Anesthesia 43: 593–598.

Nichols, R. L. and Smith, J. W. (1995) "Bacterial Contamination of an Anesthetic Agent" New Eng. J. Med., 333(3), 184–185.

PDR (1996) "Diprivan 1% Injection" Physicains' Desk Reference 1996, p. 2833.

PDR (1999) "Diprivan 1% Injection" Physicains' Desk Reference 1999.

Sandstrom et al. (1995) "Structured triglycerides were well tolerated and induced increased whole body fat oxidation compared with long-chain triglycerides in postoperative patients." JPEN J Parenter Enteral Nutr 19(5):381–6.

G. E. Sklar (1997) "Propofol and postoperative infections." Ann Pharmacother 31: 1521–3.

I. Smith, P. F. White, M. Nathanson, and R. Gouldson (1994) "Propofol—An update on its clinical use." Anesthesiology 81: 1005–1043.

Sosis, M. B. and Braverman, B. (1993) "Growth of *Staphylococcus aureus* in Four Intravenous Anesthetics" Anesth. and Anal. 77, 766–768.

Sosis, M. B., Braverman, B. and Villaflor, E. (1995) "Propofol, but not Thiopental, Supports the Growth of *Candida albicans*" Anesth. and Anal. 81, 132–134.

Stenz, R. and Bauer, K. H. (1996) "A new physiologically approached in vitro test for quick evaluation of the hemolytic activity of surfactants" Pharmazie, 51(5), 283–287.

R. D. Stark, S. M. Binks, V. N. Dukta, K. M. O'Connor, M. J. A. Arnstein, J. B. Glen (1985) "A review of the safety and tolerance of propofol ('Diprivan')." Postgrad Med J. 61 S: 152–156.

Tessler, M, Dascal, A., Gioseffini, S, Miller, M. and Mendelson, J. (1992) "Growth curves of *Staphyloccoccus aureus, Candida albicans* and *Moraxella osloensis* in propofol and other media" Can. J. Anaesth. 39(5), 509–511.

H. G. Weder "Propofol Nanodispersions." PCT Patent Application WO9710814. Mar. 27 1997.

P. F. White and J. B. Negus (1991) "Sedative infusions during local and regional anesthesia: A comparison of midazolam and propofol." J. Clin. Anesth 3: 32–39.

What is claimed is:

1. A method of reducing or substantially completely eliminating irritation around the site of injection upon injection of a formulation containing propofol comprising: administering as a bolus intravenous injection or as an intravenous infusion at the injection site, a stable, sterile and antimicrobial aqueous dispersion comprising a water-insoluble microdroplet matrix of mean diameter from about 50 nm to about 1000 nm consisting essentially of about 1% to about 15% of propofol, 1% up to about 7% of a propofol-soluble diluent, and about 0.8% to about 4% of a surface stabilizing agent, and an aqueous phase comprising a pharmaceutically acceptable water-soluble polyhydroxy tonicity modifier in a quantity sufficient to render the final composition isotonic with blood, wherein the dispersion is devoid of additional bactericidal or bacteriostatic preservative agents.

2. The method of claim 1, wherein the ratio of propofol to diluent is about 1:4 to about 1:0.1.

3. The method of claim 1, wherein the ratio of propofol to amphiphilic agent is about 1:0.8 to about 1:2.5.

4. The method of claim 1, wherein the dispersion has a viscosity of from about 1.5 to about 8 centipoise.

5. The method of claim 1, wherein the ratio of propofol to diluent is about 1:4 to about 1:0.1, and the ratio of propofol to amphiphilic agent is about 1:0.8 to about 1:2.5, and the dispersion has a viscosity of from about 1.5 to about 8 centipoise.

6. A method of inducing anesthesia or sedation comprising administering to a subject in need of same an anesthetic-inducing amount of a stable, sterile, and antimicrobial injectable aqueous dispersion of a water-insoluble microdroplet matrix of mean diameter from about 50 nm to about 1000 nm consisting essentially of about 1% to about 15% of propofol, 1% up to about 7% of a propofol-soluble diluent, and about 0.8% to about 4% of a surface stabilizing amphiphilic agent, and an aqueous phase comprising a pharmaceutically acceptable water-soluble polyhydroxy tonicity modifier in a quantity sufficient to render the final composition isotonic with blood, wherein the dispersion is devoid of additional bactericidal or bacteriostatic preservative agents.

7. The method of claim 6, wherein the ratio of propofol to diluent is about 1:4 to about 1:0.1.

8. The method of claim 6, wherein the ratio of propofol to amphiphilic agent is about 1:0.8 to about 1:2.5.

9. The method of claim 6, wherein the dispersion has a viscosity of from about 1.5 to about 8 centipoise.

10. The method of claim 6, wherein the ratio of propofol to diluent is about 1:4 to about 1:0.1, and the ratio of propofol to amphiphilic agent is about 1:0.8 to about 1:2.5, and the dispersion has a viscosity of from about 1.5 to about 8 centipoise.

11. The method of claim 1 or 6, wherein the propofol-soluble diluent is selected from the group consisting of isopropyl myristate, cholesteryl oleate, ethyl oleate, squalene, squalane, alpha-tocopherol, triglycerides of medium chain fatty acids, and combinations thereof.

12. The method of claim 1 or 6, wherein the propofol-soluble diluent is selected from the group consisting of pharmaceutically acceptable natural triglycerides from vegetable sources, pharmaceutically acceptable natural triglycerides from animal sources, pharmaceutically acceptable vegetable oils, omega-3 polyunsaturated fish oils, and combinations thereof.

13. The method of claim 1 or 6, wherein the surface stabilizing amphiphilic agent is selected from the group consisting of 1,2-dimyristoyl-sn-glycero-3-phosphocholine, 1,2-dimyristoyl-sn-glycero-3-[phospho-rac-(1-glycerol)], egg lecithin, egg phosphatidylcholine, soy phosphatidyicholine, saturated soy phosphatidyicholine, soy lecithin, dimyristoylphosphatidylcholine, dimyristoylphosphatidylglycerol, hydrogenated lecithin, and combinations thereof.

14. The method of claim 1 or 6, wherein the tonicity modifier is selected from the group consisting of sucrose, dextrose, trehalose, mannitol, lactose, glycerol, and combinations thereof.

15. The method of claim 1 or 6, wherein the dispersion is suitable for intravenous injection.

16. The method of claim 1 or 6, wherein propofol is present in an amount of about 2% by weight of the dispersion.

17. The method of claim 1 or 6, wherein the propofol-soluble diluent is a triglyceride of medium chain fatty acids.

18. The method of claim 1 or 6, wherein the polyhydroxy tonicity modifier is mannitol.

19. The method of claim 1 or 6, wherein the propofol concentration is about 2%, the propofol-soluble diluent is a triglyceride of medium chain fatty acids, the polyhydroxy tonicity modifier is mannitol, and the surface stabilizing amphiphilic agent is egg lecithin.

20. The method of claim 1 or 6, wherein propofol is present in an amount of about 2% to 5% by weight of the dispersion.

21. The method of claim 1 or 6, wherein the polyhydroxy additive is present in an amount of about 2.5% to about 20% by weight of the dispersion.

22. The method of claim 18, wherein mannitol is present in an amount of about 5.5% by weight of the dispersion.

23. The method of claim 1 or 6, wherein the propofol-soluble diluent is a mixture of medium-chain triglycerides.

24. The method of claim 23, wherein the triglyceride is a triglyceride of medium-chain fatty acids of synthetic or natural origin.

25. The method of claim 23, wherein the triglyceride is present in an amount of 2% to 6% by weight of the dispersion.

26. The method of claim 17, wherein the triglyceride is a triglyceride of medium-chain fatty acids of synthetic or natural origin.

27. The method of claim 17, wherein the triglyceride is present in an amount of 2% to 6% by weight of the dispersion.

28. The method of claim 17, wherein the triglyceride is present in an amount of 2% to 4% by weight of the dispersion.

29. The method of claim 28, wherein the triglyceride is present in an amount of 4% by weight of the dispersion.

30. The method of claim 23, wherein the mixture of medium-chain triglycerides is present in an amount of 4% by weight of the dispersion.

31. The method of claim 1 or 6, wherein the amphiphilic agent is egg lecithin.

32. The method of claim 31, wherein the egg lecithin is present in an amount of about 1% to 3% by weight of the dispersion.

33. The method of claim 32, wherein the egg lecithin is present in an amount of 1.6% by weight of the dispersion.

34. The method of claim 1 or 6, which includes dimyristoylphosphatidyl glycerol.

35. The method of claim 34, wherein the dimyristoylphosphatidyl glycerol is present in an amount of 0.05% to 0.25% by weight of the dispersion.

36. The method of claim 35, wherein the dimyristoylphosphatidyl glycerol is present in an amount of 0.1% by weight of the dispersion.

37. The method of claim 6, which includes egg lecithin and dimyristoylphosphatidyl glycerol.

38. The method of claim 37, wherein the egg lecithin is present in an amount of about 1% to 3% by weight of the dispersion and the dimyristoylphosphatidyl glycerol is present in an amount of 0.05% to 0.25% by weight of the dispersion.

39. The method of claim 38, wherein the egg lecithin is present in an amount of 1.6% by weight of the dispersion and the dimyristoylphosphatidyl glycerol is present in an amount of 0.1% by weight of the dispersion.

40. The method of claim 6, wherein the pH of the composition is about 4 to about 9.

41. The method of claim 6, wherein the pH of the composition is about 5 to about 8.

42. The method of claim 1 or 6, wherein the dispersion is sealed in a glass vial under nitrogen with a stopper.

43. The method of claim 1 or 6, wherein the dispersion is sealed in a glass vial under an inert atmosphere with a stopper.

44. The method of claim 42, wherein the dispersion is filled to about 70–90% volume capacity in the glass vial.

45. The method according to claim 1 or 6, wherein the dispersion is steam sterilizable.

46. A method of inducing anesthesia or sedation, comprising administering to a subject in need of same an anesthetic-inducing amount of a stable, sterile, and injectable aqueous dispersion of a water-insoluble microdroplet matrix of mean diameter from about 50 nm to about 1000 nm, the dispersion consisting essentially of:

(a) between about 1% to about 15% of propofol;
(b) between about 1% to about 8% of a propofol-soluble diluent;
(c) between about 0.5% to about 5% of a surface stabilizing amphiphilic agent;
(d) a pharmaceutically acceptable water-soluble polyhydroxy additive that acts as a tonicity modifier in the dispersion's aqueous phase; and
(e) water;
(f) provided the ratio of propofol to diluent is about 1:4 to about 1:0.1 and the ratio of propofol to amphiphilic agent is about 1:0.8 to about 1:2.5, and the composition has a viscosity of from about 0.8 to about 15 centipoise, wherein the dispersion prevents microbial growth, defined as no more than 0.5 log increase from the initial inoculum, of each of *Staphylococcus aureus, Escherichia coli, Pseudomonas aeruginosa, Candida albicans,* and *Aspergillus niger* for at least 7 days as measured by a test wherein a washed suspension of each of said organisms is added to a separate aliquot of said dispersion at approximately 1000 colony forming units per mL, at a temperature in the range of 20–25° C., whereafter said aliquots are incubated at 20–25° C. and are tested for viability of the microorganisms in the inoculated dispersion as determined by counting the colonies of said organism after 24, 48 hours and 7 days; and results in no irritation at the site of injection as evidenced by a test wherein said dispersion is administered as a single daily bolus injection of 12.5 mg/kg, given on the basis of body weight, for 2 successive days over a period of approximately 30 seconds, in the caudal vein of a rat such that no visual increase in the diameter of the rat tail is noted after 48 hours post injection.

47. The method of claim 46, wherein the surface stabilizing amphiphilic agent is a surface modifier selected from the group consisting of ionizable phospholipid, non-ionizable phospholipid, a mixture of ionizable phospholipid and cholesterol, a mixture of non-ionizable phospholipid and cholesterol, and mixtures thereof.

48. The method of claim 46, wherein the propofol-soluble diluent is selected from the group consisting of a synthetic fatty acid triglyceride, a natural fatty acid triglyceride, and mixtures thereof.

49. The method of claim 46, wherein the ratio of propofol to the propofol-soluble diluent is from about 1:3 to about 1:0.5.

50. The method of claim 46, wherein the ratio of propofol to the propofol-soluble diluent is from about 1:2 to about 1:1.

51. The method of claim 46, wherein the propofol-soluble diluent is a mixture of medium-chain triglyceride and vegetable oil.

52. The method of claim 51, wherein the ratio of medium-chain triglyceride to vegetable oil is from 1:3 to 3:1.

53. The method of claim 46, wherein the composition contains about 2% to about 10% of propofol.

54. The method of claim 46, wherein the pharmaceutically acceptable water-soluble polyhydroxy additive provides the propofol-containing dispersion or composition with an osmolality of about 250 to about 700 milliosmolal.

55. The method of claim 54, wherein the osmolality is about 300 to about 500 milliosmolal.

56. The method of claim 46, wherein the viscosity is from about 2 to about 5 centipoise.

57. A method of causing no irritation at the site of injection upon injection of an injectable, stable, sterile, and antimicrobial aqueous dispersion comprising a water-insoluble microdroplet matrix of mean diameter from about 50 nm to about 1000 nm, the dispersion being capable of inhibiting the growth of microorganisms and consisting essentially of about 1% to about 15% of propofol, up to about 7% of a propofol-soluble diluent, and about 0.8% to about 4% of a surface stabilizing amphiphilic agent, water, and an aqueous phase comprising a pharmaceutically acceptable water-soluble polyhydroxy tonicity modifier, the dispersion being devoid of additional bactericidal or bacteriostatic preservative agents.

58. The method of claim 57, where the propofol and diluent are present in a ratio of about 1:4 to about 1:0.1 of propofol to diluent.

59. The method of claim 57, where the propofol and amphiphilic agent are present in a ratio of about 1:0.8 to about 1:2.5 of propofol to amphiphilic agent.

60. The method of claim 57 that has a viscosity of from about 0.8 to about 15 centipoise.

61. The method of claim 57, wherein the propofol-soluble diluent is selected from the group consisting of a pharmaceutically acceptable saturated fatty acid triglyceride, a pharmaceutically acceptable unsaturated fatty acid triglyceride, and mixtures thereof.

62. The method of claim 57, wherein the propofol-soluble diluent is selected from the group consisting of pharmaceutically acceptable esters of medium chain fatty acids, pharmaceutically acceptable esters of long chain fatty acids, pharmaceutically acceptable triglycerides of medium chain fatty acids, and mixtures thereof.

63. The method of claim 57, wherein the propofol-soluble diluent is selected from the group consisting of isopropyl myristate, cholesteryl oleate, ethyl oleate, squalene, squalane, alpha-tocopherol, and mixtures thereof.

64. The method of claim 57, wherein the propofol-soluble diluent is a mixture of medium-chain triglyceride and vegetable oil.

65. The method of claim 64, wherein the ratio of medium-chain triglyceride to vegetable oil is from 1:3 to 3:1.

66. The method of claim 57, which contains about 2% to about 10% of propofol.

67. The method of claim 57, wherein the surface stabilizing amphiphilic agent is a surface modifier selected from the group consisting of ionizable phospholipid, non-ionizable phospholipid, a mixture of ionizable phospholipid and cholesterol, a mixture of non-ionizable phospholipid and cholesterol, and mixtures thereof.

68. The method of claim 57, wherein the surface stabilizing amphiphilic agent is selected from the group consisting of charged phospholipid of natural sources, uncharged phospholipid of natural sources, hydrogenated lecithin, a synthetic phospholipid, a poloxamer, a poloxamine, a polyoxyethylene sorbitan ester, and mixtures thereof.

69. The method of claim 57, wherein the surface stabilizing amphiphilic agent is a combination of cholesterol and one or more charged or uncharged phospholipids of natural sources, hydrogenated lecithin, or synthetic phospholipids.

70. The method of claim 57, wherein the surface stabilizing amphiphilic agent is selected from the group consisting of 1,2-dimyristoyl-sn-glycero-3-phosphatidylcholine, 1,2-dimyristoyl-sn-glycero-3-[phospho-rac-(1-glycerol)], egg lecithin, egg phosphatidylcholine, soy phosphatidylcholine, saturated soy phosphatidylcholine, soy lecithin, dimyristoylphosphatidylcholine, and dimyristoylphosphatidylglycerol.

71. The method of claim 57, wherein the dispersion elicits an anesthetic effect in a warm-blooded animal and human subject upon intravenous administration.

72. The method of claim 57, wherein the tonicity modifier is selected from the group consisting of sucrose, dextrose, trehalose, mannitol, lactose, glycerol, and mixtures thereof.

73. The method of claim 57, wherein the dispersion is isotonic with blood.

74. The method of claim 57, wherein the dispersion is suitable for intravenous injection.

75. The method of claim 57, wherein the dispersion contains a pharmaceutically acceptable water-soluble polyhydroxy tonicity modifier in an amount sufficient to provide an osmolality of about 250 to about 700 milliosmolal.

76. The method of claim 75, wherein the osmolality is about 300 to about 500 milliosmolal.

77. The method of claim 57, wherein the dispersion has a viscosity from about 2 to about 5 centipoise.

78. The method of claim 6, wherein inducing anesthesia comprises producing and maintaining at least one of ambulatory anesthesia, neurosurgical anesthesia, pediatric anesthesia, monitored anesthetic care, intensive care sedation, chronic sedation, general anesthesia, low dose sedation, and long-term sedation.

79. A method of inducing anesthesia or sedation, comprising administering to a subject in need of same an anesthetic-inducing amount of a stable, sterile, and injectable aqueous dispersion of a water-insoluble microdroplet matrix having a mean diameter of about 50 nm to about 1000 nm, the dispersion consisting essentially of:
  (a) propofol in an amount from about 1% to about 15% by weight of the dispersion;
  (b) a propofol-soluble diluent in an amount from about 1% to about 8% by weight of the dispersion;
  (c) a surface stabilizing amphiphilic agent in an amount from about 0.5% to about 5% by weight of the dispersion;
  (d) a pharmaceutically acceptable water-soluble polyhydroxy additive in the dispersion's aqueous phase; and
  (e) water;
  provided the ratio of propofol to diluent is about 1:4 to about 1:0.1 and the ratio of propofol to amphiphilic agent is about 1:0.8 to about 1:2.5 and the composition has a viscosity of about 0.8 to about 15 centipoise;
  wherein the dispersion prevents microbial growth of no more than 0.5 log increase from the initial inoculum, of any one of *Staphylococcus aureus, Eseherichia coli, Pseudomonas aeruginosa, Candida albicans,* and *Aspergillus niger* for at least 7 days as measured by a test wherein a washed suspension of the microbe is added to an aliquot of said dispersion at approximately 1000 colony forming units per mL, at a temperature in the range of 20–25° C., whereafter said aliquot is incubated at 20–25° C. and tested for viability of the microbe in the inoculated dispersion as determined by counting the colonies of the microbe after 24 hours, 48 hours, and 7 days; and
  wherein the dispersion results in no irritation at the site of injection as evidenced by a test wherein said dispersion is administered as a single daily bolus injection of 12.5 mg/kg, given on the basis of body weight, for 2 successive days over a period of approximately 30 seconds, in the caudal vein of a rat such that no visual increase in the diameter of the rat tail is noted after 48 hours post injection.

80. A method of inducing anesthesia or sedation, comprising administering to a subject in need of same an anesthetic-inducing amount of a stable, sterile, and injectable aqueous dispersion of a water-insoluble microdroplet matrix having a mean diameter of about 50 nm to about 1000 nm, the dispersion consisting essentially of:
- (a) propofol in an amount of about 2% by weight of the dispersion;
- (b) one or more medium-chain triglycerides in an amount of 4% by weight of the dispersion;
- (c) egg lecithin in an amount of 1.6% by weight of the dispersion;
- (d) dimyristoylphosphatidyl glycerol in an amount of 0.1% by weight of the dispersion;
- (e) mannitol in the dispersion's aqueous phase in an amount of 5.5% by weight of the dispersion; and
- (f) water.

81. The method of claim 80, wherein the one or more medium-chain triglycerides are of synthetic or natural origin.

82. The method of claim 80, wherein the dispersion is sealed in a glass vial under nitrogen with a stopper.

83. The method of claim 80, wherein the dispersion is sealed in a glass vial under an inert atmosphere with a stopper.

84. The method of claim 82, wherein the dispersion is filled to about 70–90% volume capacity in the glass vial.

85. The method of claim 80, wherein the dispersion is steam sterilizable.

86. A method of inducing anesthesia or sedation, comprising administering to a subject in need of same an anesthetic-inducing amount of an injectable, stable, sterile, and antimicrobial aqueous dispersion comprising a water-insoluble microdroplet matrix having a mean diameter of about 50 nm to about 1000 nm capable of inhibiting the growth of microorganisms, the dispersion consisting essentially of:
- propofol in an amount of about 2% by weight of the dispersion;
- one or more medium-chain triglycerides in an amount of 4% by weight of the dispersion;
- egg lecithin in an amount of 1.6% by weight of the dispersion;
- dimyristoylphosphatidyl glycerol in an amount of 0.1% by weight of the dispersion; and
- mannitol in the dispersion's aqueous phase in an amount of 5.5% by weight of the dispersion;
- wherein the dispersion is devoid of additional bactericidal or bacteriostatic preservative agents and causes no irritation at the site of injection.

87. The method of claim 86, wherein the one or more medium chain triglycerides are of synthetic or natural origin.

88. The method of claim 86, wherein the dispersion is sealed in a glass vial under nitrogen with a stopper.

89. The method of claim 86, wherein the dispersion is sealed in a glass vial under an inert atmosphere with a stopper.

90. The method of claim 88, wherein the dispersion is filled to about 70–90% volume capacity in the glass vial.

91. The method of claim 86, wherein the dispersion is steam sterilizable.

* * * * *